United States Patent [19]
Knopp et al.

[11] Patent Number: 6,016,811
[45] Date of Patent: Jan. 25, 2000

[54] METHOD OF USING A MICROWAVE ABLATION CATHETER WITH A LOOP CONFIGURATION

[75] Inventors: Peter G. Knopp, Fremont, Calif.; Eugene Downar, Toronto, Canada; Robert E. Woodard, Hayward; Kevin T. Larkin, Menlo Park, both of Calif.

[73] Assignee: Fidus Medical Technology Corporation, Fremont, Calif.

[21] Appl. No.: 09/144,725

[22] Filed: Sep. 1, 1998

[51] Int. Cl.[7] ................................................. A61B 17/39
[52] U.S. Cl. ........................... 128/898; 607/156; 607/101; 607/122
[58] Field of Search ................... 606/41, 42, 45, 606/48–50; 607/100–102, 115, 116, 122, 154, 156; 128/898

[56] References Cited

U.S. PATENT DOCUMENTS

| | | | |
|---|---|---|---|
| 5,150,717 | 9/1992 | Rosen et al. | 607/156 |
| 5,370,644 | 12/1994 | Langberg | 606/33 |
| 5,575,811 | 11/1996 | Reid et al. | 607/101 |
| 5,741,249 | 4/1998 | Moss et al. | 606/33 |

*Primary Examiner*—Michael Peffley
*Attorney, Agent, or Firm*—Beyer & Weaver, LLP

[57] ABSTRACT

A catheter which may be configured as a loop during an ablation procedure, and a method of use for such a catheter, are disclosed. According to one aspect of the present invention, a method for medical treatment using an ablation catheter system that includes a catheter with a transmission line disposed within a flexible tubular member and a transducer that is located at a central portion of the catheter that is proximal to a distal tip portion of the catheter involves introducing the catheter into a first vessel of the body of a patient and past the heart of the patient such that the distal tip portion of the catheter at least partially passes out of the body through a second vessel while the central portion of the catheter is positioned within a cardiac chamber. Curvature, which includes the central portion of the catheter, is then formed in the catheter within the cardiac chamber, and electromagnetic energy is applied to the transmission line to cause ablation of cardiac tissue in a region adjacent to the central portion of the catheter. In one embodiment, a loop which includes the central portion of the catheter is formed within the cardiac chamber.

21 Claims, 12 Drawing Sheets

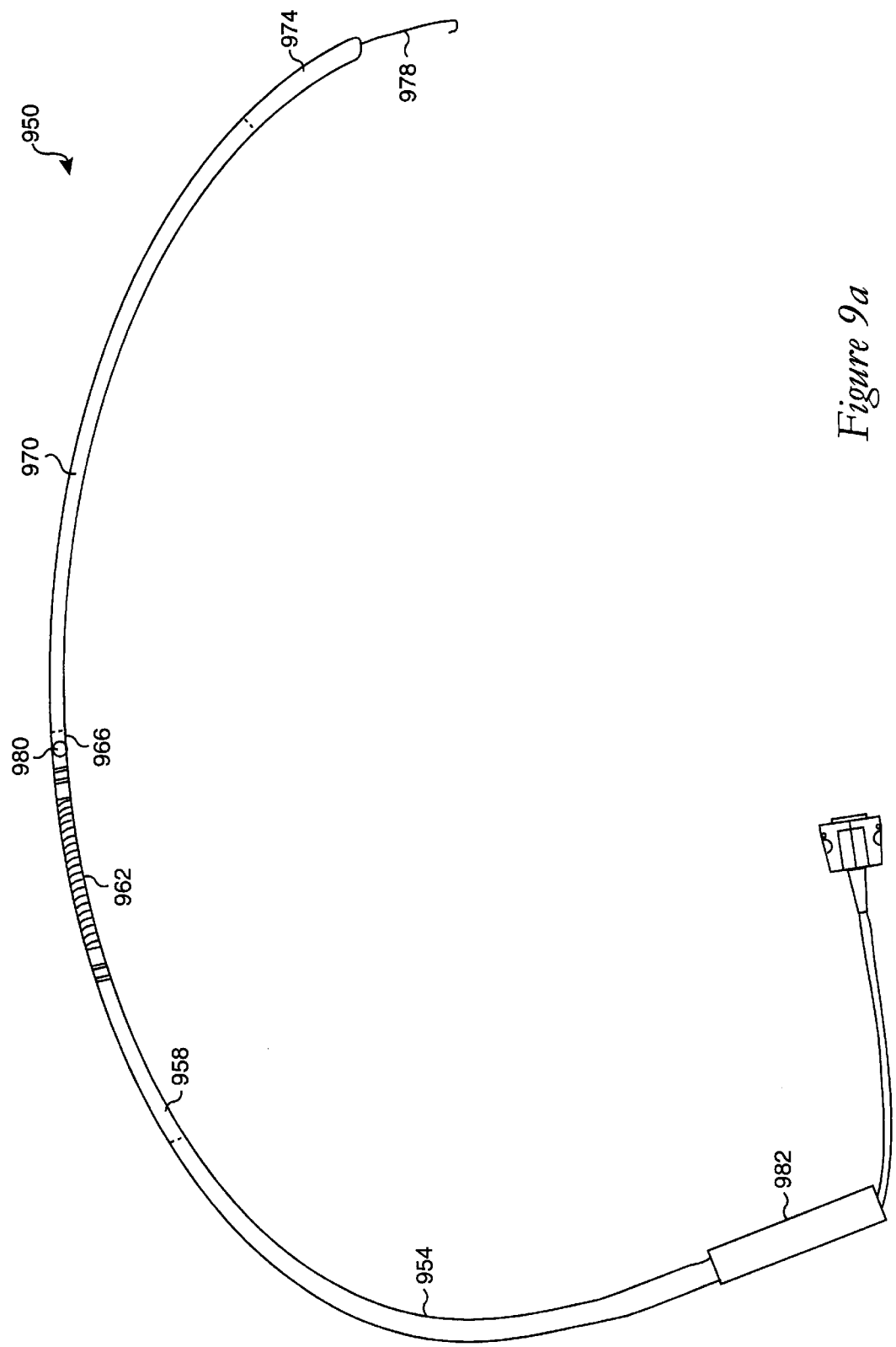

METHOD OF USING A MICROWAVE ABLATION CATHETER WITH A LOOP CONFIGURATION

CROSS-REFERENCE TO RELATED APPLICATION

The present invention is related to U.S. patent application Ser. No. 09/144,962, filed Sep. 1, 1998, which is incorporated herein by reference in its entirety.

BACKGROUND OF THE INVENTION

1. Field of Invention

The present invention relates generally to ablation catheter systems that use electromagnetic energy in the microwave frequency range to ablate internal bodily tissues. More particularly, the present invention relates to methods of using a microwave ablation catheter which may be manipulated to form a loop within a cardiac chamber to facilitate the ablation of cardiac tissue.

2. Description of the Related Art

Catheter ablation is a therapy that is becoming more widely used for the treatment of medical problems such as cardiac arrhythmias, cardiac disrhythmias, and tachycardia. Most presently approved ablation catheter systems utilize radio frequency (RF) energy as the ablating energy source. However, RF energy has several limitations which include the rapid dissipation of energy in surface tissues. This rapid dissipation of energy often results in shallow "burns," as well as a failure to access deeper arrhythmic tissues. As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and the preheating of blood prior to infusions. Catheters which utilize microwave energy have been observed to be capable of generating substantially larger lesions than those generated by RF catheters, which greatly simplifies the actual ablation procedures. Some catheter systems which utilize microwave energy are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stem, et al., each of which is incorporated herein by reference in its entirety.

Cardiac arrhythmias, which may be treated using catheter ablation, are generally circuits, known as "arrhythmia circuits," which form within the chambers of the heart. As is known to those skilled in the art, arrhythmia circuits are abnormal electrical connections which may form in various areas of the heart. For example, arrhythmia circuits may form around veins and/or arteries which lead away from and to the heart. Cardiac arrhythmias may occur in any area of the heart where arrhythmia circuits are formed.

Atrial fibrillation is one type of cardiac arrhythmia which may be treated using catheter ablation. For atrial fibrillation, which occurs in the left side of the heart, arrhythmia circuits form within the atria and between pulmonary veins. Due to the fact that these arrhythmia circuits often prevent the heart from beating normally, cutting the arrhythmia circuits is necessary to restore a normal heart beat. Many different cutting patterns may generally be implemented to cut arrhythmia circuits and, specifically, arrhythmia circuits formed within the left side of the heart. By way of example, a cutting pattern which involves the formation of a series of perpendicular, linear lesions may be used to cut circuits formed between pulmonary veins. When atrial fibrillation occurs in the right side of the heart, the cause of the atrial fibrillation is typically related to damage to cardiac tissue. In some cases, the atrial fibrillation may be attributed to scar tissue formed in the right side of the heart.

In order to properly position a conventional radio frequency catheter to form a desired cutting pattern, a catheter often must be repositioned for each ablation process, i.e., each time an overall linear lesion is to be formed. As will be appreciated by those skilled in the art, the tip of a catheter must often be repositioned in order to form a linear lesion. As the tip may only ablate a relatively small portion of tissue at a time, the tip must generally be moved, e.g., incrementally or point to point, in order for an overall linear lesion to be formed. That is, the process of placing an ablating tip in a desired position, then performing ablation, is typically repeated in order to form an overall lesion. In the event that ablation is occurring through a substantial amount of blood, coagulum may form on the tip. When too much coagulum forms, it may be necessary to remove the catheter from the body of the patient for cleaning, thereby requiring a reinsertion of the catheter to continue an overall ablation procedure. Reinserting the catheter into the body of a patient is often painful and time-consuming, especially if reinsertion occurs often.

While some microwave antenna catheters, as for example those with a steerable shaft, may effectively be positioned at any position within a heart, the antenna portion of the catheter may not be aligned in a desired direction. In other words, substantially any portion of the heart may be reached for ablation, although the antenna portion may not be oriented in a position or direction that enables a single linear lesion to be formed such that the desired tissue is ablated at one time.

Therefore, what is desired is a catheter with an antenna portion that may be readily conformed to and placed against the wall of a cardiac chamber such that a linear lesion may be formed. Specifically, what is desired is a manipulatable catheter with an antenna portion which may be readily positioned in substantially any orientation, e.g., an antenna portion that makes a line at any angle relative to a chosen planed in the heart, as well as a method for using such a catheter.

SUMMARY OF THE INVENTION

The present invention relates to methods of using a catheter which may be configured as a loop during an ablation procedure. According to one aspect of the present invention, a method for medical treatment using an ablation catheter system that includes a catheter with a transmission line disposed within a flexible tubular member and a transducer that is located at a central portion of the catheter that is proximal to a distal tip portion of the catheter involves introducing the catheter into a first vessel of the body of a patient and past the heart of the patient such that the distal tip portion of the catheter at least partially passes out of the body through a second vessel while the central portion of the catheter is positioned within a cardiac chamber. Curvature, which includes the central portion of the catheter, is then formed in the catheter within the cardiac chamber, and electromagnetic energy is applied to the transmission line to cause ablation of cardiac tissue in a region adjacent to the central portion of the catheter.

In one embodiment, a loop which includes the central portion of the catheter is formed within the cardiac chamber.

In such an embodiment, the method may include modifying the loop in the catheter within the cardiac chamber such that the size of the loop is altered.

According to another aspect of the present invention, a method for medical treatment involves using an ablation catheter system that includes a catheter with a transmission line disposed within a flexible tubular member of the catheter and a transducer coupled to the transmission line of the catheter. The transducer is arranged to generate an electric field sufficiently strong to cause tissue ablation, and is located at a central section of the catheter that is proximal to a distal section of the catheter. The method includes introducing a tip of the distal section of the catheter into a first vessel of the body of a patient, maneuvering the tip of the distal section of the catheter through the first vessel and into a cardiac chamber of the body of the patient, maneuvering the tip of the distal section of the catheter past the cardiac chamber and into a second vessel of the body of the patient, and maneuvering the tip of the distal section of the catheter through the second vessel such that the central section of the catheter is positioned within the cardiac chamber.

In one embodiment, maneuvering the tip of the distal section of the catheter through the second vessel includes maneuvering the tip of the distal section of the catheter out of the body through the second vessel. In such an embodiment, the method may also involve imparting a force to at least one of a proximal end of the catheter and the distal section of the catheter, the proximal end of the catheter being proximal to the central section of the catheter, the proximal end of the catheter further being external to the body while the central section of the catheter is positioned within the cardiac chamber.

These and other advantages of the present invention will become apparent upon reading the following detailed descriptions and studying the various figures of the drawings.

BRIEF DESCRIPTION OF THE DRAWINGS

The invention may best be understood by reference to the following description taken in conjunction with the accompanying drawings in which:

FIG. 9a is a diagrammatic representation of a catheter that includes a hinge in accordance with a fourth embodiment of the present invention.

DETAILED DESCRIPTION OF THE EMBODIMENTS

The incremental positioning of a conventional catheter within a patient during an overall ablation process is often necessary to facilitate the formation of a linear lesion within a cardiac chamber. When a catheter is repeatedly repositioned within the body of a patient during an overall ablation procedure, the patient may experience discomfort. Repeatedly repositioning a catheter is further undesirable due to the fact that such repetition is inefficient and time-consuming. In addition, conforming the tip of a conventional catheter to a cardiac chamber in a desired direction, or orientation, may be difficult, as the tip may not be readily manipulated. As such, the catheter tip, which contains an antenna, may not be properly conformed against the wall of a cardiac chamber to form a desired linear lesion.

A catheter that has an antenna section, or portion, which may be manipulated essentially from both ends of the antenna allows the antenna to be readily conformed to the wall of a cardiac chamber during ablation. In other words, a catheter with an antenna that is not located at the tip portion of the catheter may be conformed against the wall of a cardiac chamber at any point and with effectively any direction orientation by manipulating both ends of the catheter. Specifically, a force may be applied to at least one end of the catheter in order to cause a loop to be formed in the catheter, i.e., a "loop" catheter. A loop, which encompasses the portion of the loop catheter with the antenna, may be formed such that the length of the antenna is conformally positioned against a wall of cardiac chamber. The ability to position the antenna such that the length of the antenna comes into substantially direct contact with a cardiac wall allows relatively even lesions to be formed during ablation. When it is desired for the position of the antenna to be moved, a force may be applied to at least one end of the loop catheter to move the antenna and, in some cases, form a loop of a different size. As such, the antenna may effectively be repositioned within a patient without removing and reinserting the loop catheter.

Figure 1:
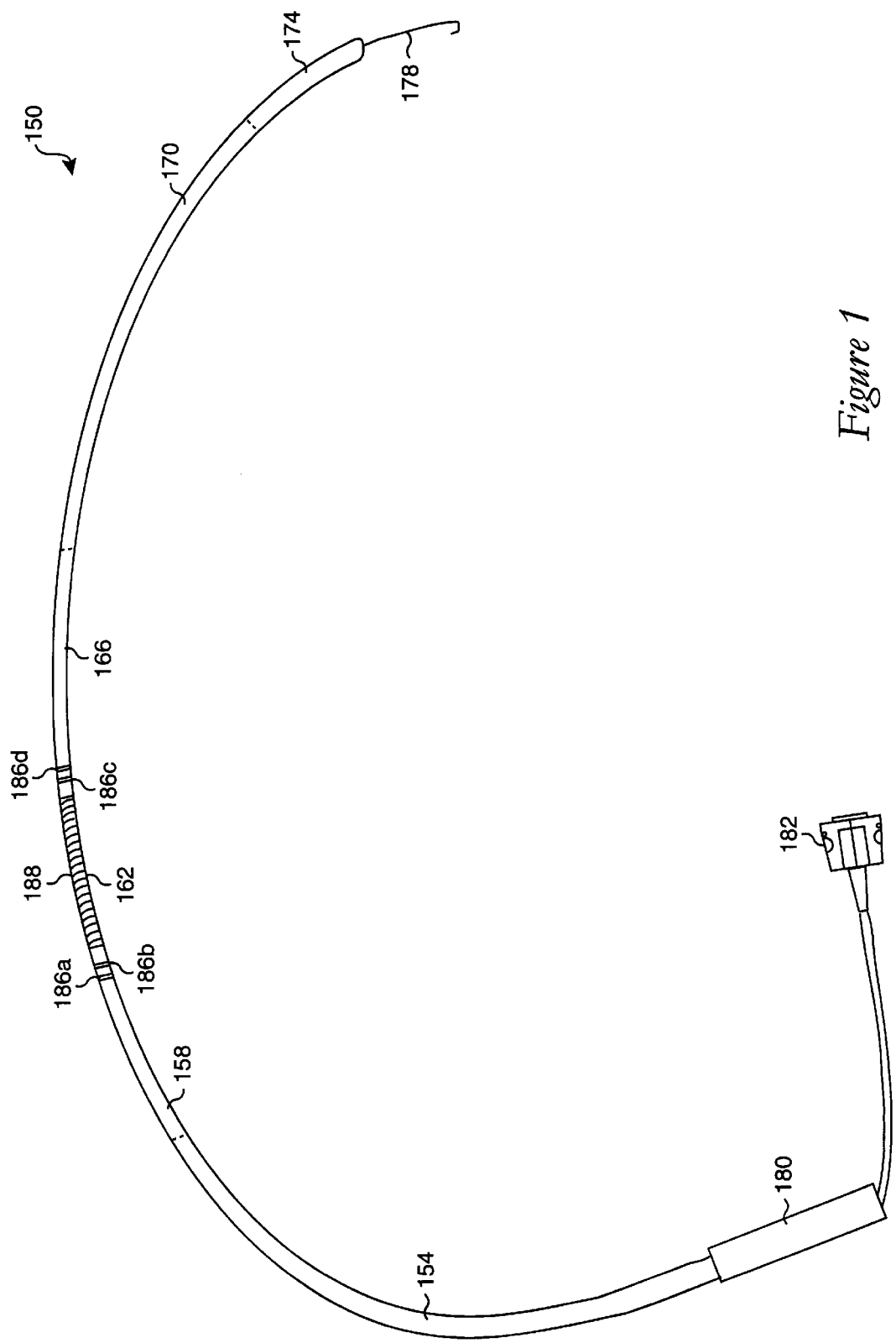
FIG. 1 is a diagrammatic representation of a loop catheter in accordance with a first embodiment of the present invention.

Referring initially to FIG. 1, a loop catheter that is suitable for use in a microwave ablation procedures will be described. FIG. 1 is a diagrammatic representation of a loop catheter, or a catheter which may be configured to include a loop, in accordance with an embodiment of the present invention. As shown, an overall loop catheter 150 includes a first proximal section 154, a second proximal section 158, an antenna section 162, a first distal section 166, a second distal section 170, a third distal section 174, and a tip section 178. It should be appreciated that the relative dimensions of the different sections of catheter 150 have not been shown to scale for purposes of illustration.

In general, the length of catheter 150 may vary widely. However, the length is typically such that catheter 150 may be readily manipulated with one end protruding from the neck of a patient, e.g., through the jugular vein, or from just under the clavicle of the patient, e.g., through the subclavian vein, and the other end protruding from the femoral vein of the patient. By way of example, the length of catheter 150 may range from approximately 150 centimeters in length to approximately 275 centimeters in length. Similarly, the thickness, e.g., diameter, of catheter 150 may also vary depending upon factors that include, but are not limited to, the materials from which catheter 150 is formed. For instance, the diameter of catheter 150 may range from approximately seven French to approximately nine French, i.e., approximately 0.092 inches to approximately 0.141 inches.

In one embodiment, first proximal section 154 is a shaft that is fabricated from a PEBAX resin which is available commercially from Elf Atochem of Germany, although first proximal section 154 may be formed from other suitable materials including, but not limited to, medical grade polyolefins, fluoropolymers, polyurethane, or polyvinylidene fluoride. In the described embodiment, first proximal section 154 is stiffened using stainless steel braided wires, or similar structures, that are arranged to allow first proximal section 154 to sustain torque. As such, first proximal section 154 may be referred to as a proximal braided section. Generally, first proximal section 154 has a relatively high durometer, as for example a durometer in the range of approximately sixty Shore D to eighty Shore D. In other words, first proximal section 154 is considered to be relatively "stiff."

A handle 180 is coupled to first proximal section 154 in order to enable catheter 150 to be gripped by a user, e.g., a person who is manipulating catheter 150. It should be appreciated, though, that in some embodiments, a handle such as handle 180 that is coupled to first proximal section 154 is not necessarily provided. In proximity to handle 180 is a connector 182 which is arranged to couple a transmission line (not shown) associated with catheter 150 to a power supply, or similar device, that is designed to generate controlled electromagnetic energy. The distance from a distal end of first proximal section 154 to connector 182 is typically greater than approximately 100 centimeters, although it should be appreciated that the distance from the distal end of first proximal section 154 to connector 182 and, hence, the length of first proximal section 154, may be widely varied.

Second proximal section 158 is coupled to a distal region of first proximal section 154. While second proximal section 158 may generally be coupled to first proximal section 154 using any suitable method, one particularly suitable method for coupling second proximal section 158 to first proximal section 154 involves heat fusion. That is, second proximal section 158 is fused to first proximal section 154. The underlying structure associated with the junction, or interface, between second proximal section 158 and first proximal section 154 will be discussed below with reference to FIG. 4a.

Like first proximal section 154, second proximal section 158 is typically a shaft that is formed from a material such as a PEBAX resin, which may be referred to herein and after as "PEBAX." However, second proximal section 158 generally has a lower stiffness than first proximal section 154, due to the fact that second proximal section 158 is arranged to be substantially bent in the formation of a loop in catheter 150. In other words, second proximal section 158 is generally more flexible than first proximal section 154. As such, while first proximal section 154 may effectively be stiffened with stainless steel braided wires, second proximal section 158 is not stiffened by such wires. Therefore, second proximal section 158 may generally be referred to as a proximal unbraided section. While the durometer of second proximal section 158 may vary widely, the durometer of second proximal section 158 is often in the range of approximately thirty Shore D to approximately seventy Shore D. Likewise, the length of second proximal section 158 may also vary. By way of example, the length of second proximal section 158 may be in the range of approximately three centimeters to approximately ten centimeters.

Proximal electrode bands 186a, 186b are located at a distal portion of second proximal section 158, and are arranged to detect electro-physiological signals from cardiac tissue. Therefore, electrode bands 186a, 186b may be used to map the relevant region of the heart, i.e., the portion of the heart with which an ablation procedure is associated, prior to or after an ablation procedure. Although electrode bands 186a, 186b may be used to map the relevant region of the heart, in the described embodiment, electrode bands 186a, 186b are more likely to be used to aid in positioning catheter 150 during an ablation procedure. In general, electrode bands 186a, 186b may be formed from any suitable material which has biocompatible characteristics. Such materials generally include, but are not limited to, stainless steel and iridium platinum.

Second proximal section 158 interfaces antenna section 162, which, in the described embodiment, includes a helical antenna 188. The helical antenna is generally arranged to radiate electromagnetic energy, e.g., electromagnetic energy in the microwave frequency range. The overall structure of antenna section 162 will be described below with reference to FIG. 3. Antenna section 162 is arranged to bend more than second proximal section 158 and first distal section 166. That is, antenna section 162 is generally more flexible than both second proximal section 158 and first distal section 166. During an ablation procedure while catheter 150 is in a loop configuration, antenna section 162 may bend such that it basically conforms against the cardiac tissue that is being ablated. An example of a catheter formed in a loop configuration will be discussed below with respect to FIGS. 2a and 2b.

The coiled length of antenna 188 and, therefore, the length of antenna section 162 may generally be widely varied. It should be appreciated that the length of antenna section 162 is such that antenna 188 may be accommodated substantially within antenna section 162. Often, the length of antenna section 162 is dependent upon the frequency of the electromagnetic radiation. The length of antenna section 162 may typically range from approximately two centimeters in length to approximately six centimeters in length. Specifically, in one embodiment, the length of antenna section 162 may be in the range of approximately 3.9 centimeters to approximately 4.2 centimeters in length.

First distal section 166 generally has the same stiffness, and overall dimensions, as second proximal section 158. For example, first distal section 166 is typically also formed from a low-durometer PEBAX blend. In the described embodiment, first distal section 166 is formed from PEBAX which has not been stiffened by a structure such as braided wires. Therefore, first distal section 166 may be referred to as a distal unbraided section. By maintaining the same general stiffness and dimensions in first distal section 166 and second proximal section 158, the flexibility of catheter 150 may be symmetric with respect to antenna section 162. Such symmetry allows a loop, which includes first distal section 166, antenna section 162, and second proximal section 158, to be readily formed. Distal electrode bands 186c, 186d are located at a proximal portion of first distal section 166. Like electrode bands 186a, 186b, which were previously discussed, electrode bands 186c, 186d may be formed from biocompatible materials such as stainless steel and iridium platinum, and are arranged to detect electrophysiological signals from cardiac tissue.

As shown, first distal section 166 interfaces with second distal section 170, which has a stiffness that is approximately the same as the stiffness of first proximal section 154. In one embodiment, first distal section 166 may be heat fused to second distal section 170. The overall junction between first distal section 166 and second distal section 170 will be discussed below with respect to FIG. 4b. Second distal section 170 generally has the same external structure as first proximal section 154, e.g., second distal section 170 may be formed from a PEBAX shaft whose torque characteristics are improved by using stainless steel braid wires. Hence, second distal section 170 may also be considered to be a distal braided section of catheter 150. Although the overall length of second distal section 170 may vary widely, the length is often greater than approximately thirty centimeters.

Third distal section 174, which may be heat fused or otherwise generally coupled to second distal section 170, is often more flexible than second distal section 170. As such, in one embodiment, third distal section 174 is formed from a PEBAX shaft that is not reinforced with braided wires. While the length of third distal section 174 may vary, the length is typically in the range of approximately three centimeters to approximately ten centimeters, e.g., approximately five centimeters.

In the embodiment as shown, tip section 178 is a guidewire that is bonded to third distal section 174, as will be described below with reference to FIG. 5. Third distal section 174 may be considered as an overall interface between highly flexible tip section 178 and relatively stiff second distal section 170. Tip section 178, which may be a flexible, spirally wound wire structure with gauge of approximately 0.035 inches, or approximately 0.09 centimeters, and a "J-hook" end, is arranged to be engaged by a device such as a snare. Although the length of tip section 178 may vary, tip section 178 often has a length in the range of approximately eight centimeters to approximately twelve centimeters, as measured from the distal end of third distal section 174.

Figure 2A:
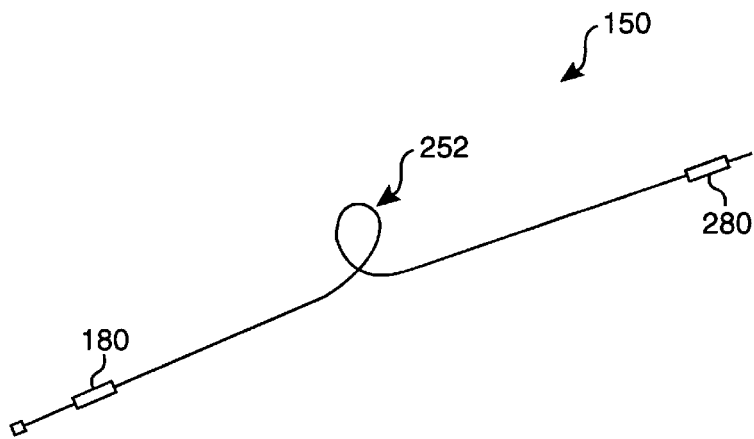
FIG. 2a is a diagrammatic representation of a loop catheter, e.g., catheter 150 of FIG. 1, arranged in a loop configuration in accordance with the first embodiment of the present invention.

As previously mentioned, catheter 150 is arranged to be formed in a loop configuration in order to facilitate the positioning of an antenna within a cardiac chamber during an ablation procedure. FIG. 2a is a diagrammatic representation of a loop catheter, e.g., catheter 150 of FIG. 1, that is arranged in a loop configuration in accordance with an embodiment of the present invention. As shown, catheter 150 includes a loop 252. It should be appreciated that for ease of illustration, catheter 150 has not been drawn to scale.

Figure 2B:
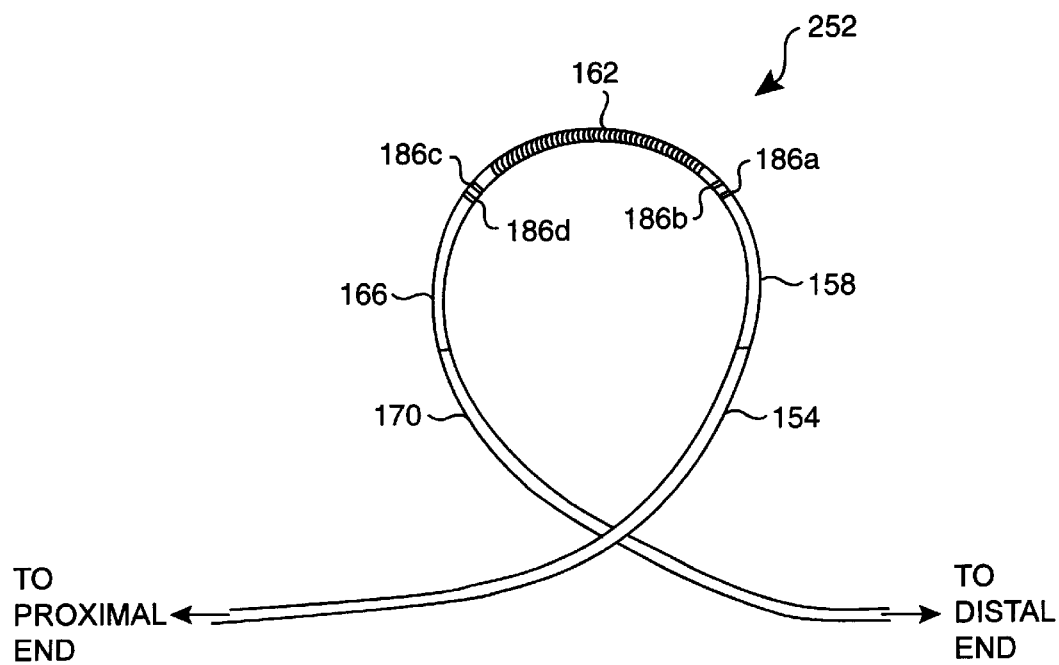
FIG. 2b is a diagrammatic close-up representation of the looped portion of loop catheter of FIG. 2a in accordance with the first embodiment of the present invention.

Loop 252, as will be discussed below with respect to FIG. 2b, is formed substantially from the antenna section, the second proximal section, and the first distal section, of catheter 150. Loop 252 may be formed by manipulating catheter 150 from its proximal end and its distal end. A handle 280, which may be mounted near the distal end of catheter 150 after the distal end of catheter 150 has been passed out of a vein such as the jugular vein, may be used in conjunction with handle 180 to enable a user to maintain a grip near both ends of catheter 150. Alternatively, handle 180 may be replaced by a handle similar to handle 280. The overall manipulation of catheter 150 such that loop 252 may be formed will be described below with reference to FIGS. 6a and 6b.

Typically, loop 252 is formed such that loop 252 is positioned within a cardiac chamber, such as the right atrium of the heart, as previously mentioned. The formation of loop 252 allows the antenna portion of the catheter to be easily conformed, and held, against the cardiac wall during ablation. FIG. 2b is a diagrammatic close-up representation of the loop 252 of FIG. 2a in accordance with an embodiment of the present invention. Loop 252 is formed from antenna section 162, second proximal section 158, and first distal section 166. Hence, antenna section 162 is curved, as are second proximal section 154 and first distal section 166. Although the curvature of each section may be substantially the same, the curvature of antenna section 162 often differs from the curvature of second proximal section 154 and first distal section 166. In general, the overall curvature, e.g., approximate diameter, of loop 252 may be varied by varying the force applied at or near the ends of catheter 150.

In general, portions of the catheter which are arranged to come into contact with the internal organs and bodily fluids of a patient are formed from biocompatible materials, or materials that do not cause reactions with internal organs or bodily fluids. The actual structure, e.g., internal structure, of a loop catheter may vary widely depending upon factors which include, but are not limited to, the materials from which the loop catheter is fabricated. As described above, one suitable loop catheter may be at least partially formed from PEBAX. The internal structure of such a loop catheter will be described below with reference to FIGS. 3, 4a, 4b, and 5. Another suitable loop catheter may be formed using a material such as polyethylene, as will be discussed below with respect to FIG. 7.

Figure 3:
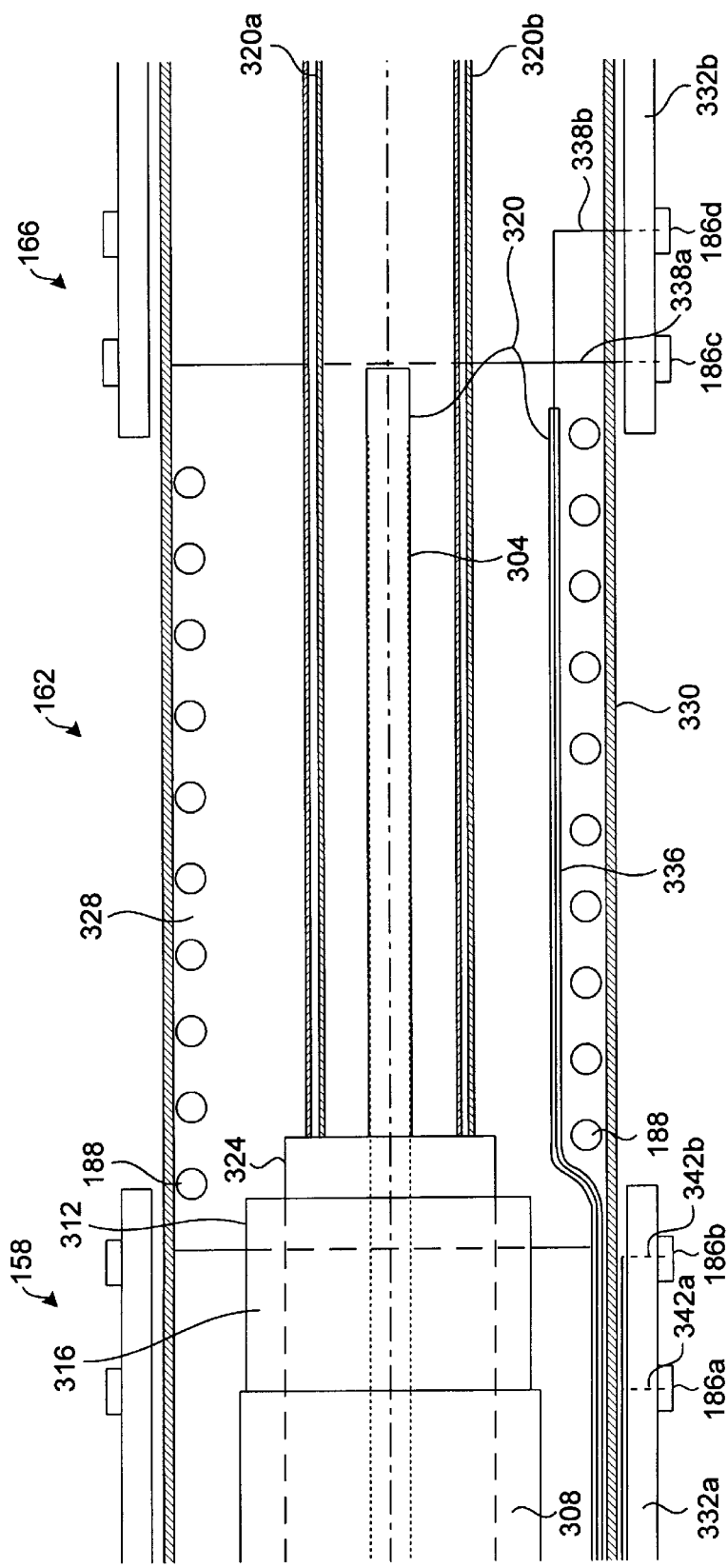
FIG. 3 is a diagrammatic longitudinal cross-sectional representation of an antenna portion of a catheter, e.g., antenna section 162 of catheter 150 as shown in FIG. 1, in accordance with the first embodiment of the present invention.

FIG. 3 is a diagrammatic representation of an antenna portion of a catheter, e.g., antenna section 162 of catheter 150 as shown in FIG. 1, in accordance with an embodiment of the present invention. It should be appreciated that antenna section 162, and components of the catheter that are located within antenna section 162, have not been shown to scale, for ease of illustration. By way of example, the spacing between some components within antenna section 162 has been exaggerated for illustrative purposes. A transmission line 308, which is typically a coaxial cable 308, includes a center conductor 304 that is disposed within antenna section 162. Transmission line 308 and, hence, center conductor 304, is arranged to be coupled to a power supply that is external to the overall catheter which includes transmission line 308. Although the outer diameter of transmission line 308 may vary, the outer diameter of transmission line 308 is typically in the range of approximately 0.088 to approximately 0.175 centimeters, e.g., 0.127 centimeters.

A proximal end 312 of antenna 188, which is typically in the form of a coil, is grounded to a shield 312 of transmission line 308. A distal end 320 of antenna 188 is attached to center conductor 304 to enable center conductor 304 to provide power to antenna 188. In one embodiment, when power is provided to antenna 188, antenna 188 radiates electromagnetic energy in the microwave frequency range. Generally, antenna 188 and center conductor 304 are aligned with the longitudinal axis of the catheter.

Antenna 188 may generally be made from any suitable material, as for example spring steel, beryllium copper, or silver-plated copper. When antenna 188 is in the form of a coil, e.g., a helical coil, the outer diameter of antenna 188 may vary to some extent based upon the particular application of the catheter. By way of example, a catheter suitable for use in an atrial fibrillation application may have coil outer diameters in the range of approximately 0.15 to approximately 0.4 centimeters. More preferably, the outer diameter of antenna 188 may be in the range of approximately 0.2 to approximately 0.3 centimeters. The overall length of antenna 188, as well as the number of turns in antenna 188, may also vary. For instance, the coiled length of antenna 188 may be in the range of approximately two to approximately six centimeters in length. In one embodiment, the coiled length of antenna 188 may be in the range of approximately 3.9 to approximately 4.2 centimeters in length. Although the number of turns in antenna 188 has been shown to be relatively small for ease of illustration, it should be appreciated that the number of turns in antenna 188 may generally be widely varied, as for example in the range of approximately sixty to approximately one hundred turns.

In order to maintain comparable stiffnesses and, hence, similar flexibilities, in second proximal section 158 and first distal section 166, first distal section 166 may be reinforced with extension tubes 320. While the number of tubes 320 used to provide stiffness in first distal section 166 may vary depending upon the materials used to fabricate tubes 320, as well as the size of tubes 320, in the described embodiment, two tubes 320a, 320b are used to stiffen first distal section 166. Tubes 320a, 320b are arranged to provide a stiffniess that is comparable to the stiffness of transmission line 308. Tubes 320a, 320b, which may be formed from a material such as Teflon or polyethylene, are arranged to abut against an inner dielectric 324 of transmission line 308, which serves to separate center conductor 304 from shield 316. Tubes 320a, 320b are further arranged such that a portion of center conductor 304 protrudes into tube 320a, which is situated within tube 320b.

As shown, antenna 188, and, hence, portions of center conductor 304 and tubes 320, are encapsulated in a dielectric material 328. That is, material 328 which both fills and surrounds antenna 188 is typically a flexible dielectric material. Suitable flexible dielectric materials include, but are not limited to, materials such as silicone. One family of silicone products which has been observed to work well is GE Liquid Injection Material (LIM) 6040 through 6070, a silicone family that is available from General Electric Company in Waterford, N.Y. In general, the outer diameter of dielectric material 328 is in the range of approximately 0.02 to approximately 0.03 centimeters greater than the outer diameter of antenna 188. Alternatively, in one embodiment, the outer diameter of dielectric material 328 is approximately the same as the outer diameter of antenna 188.

Shrink tubing 330, which may be formed from a material such as a flourinated polymer, e.g., Teflon, is used to effectively seal antenna 188, material 328, coaxial cable 308, and tubes 320. Shrink tubing 330 may serve to prevent "kinks," or crimps, from being formed in the overall catheter during bending. Although the thickness of shrink tubing 330 may vary widely, the thickness of shrink tubing 330 generally varies between approximately 0.005 and approximately 0.02 centimeters.

As mentioned above, electrode rings 186 are located on second proximal section 158 and first distal section 166, and may be used to map the relevant region of the heart prior to or after an ablation procedure. Specifically, electrode rings 186 are positioned along the outer diameter of tubes 332, e.g., tubes of unbraided PEBAX, that form the external structure of second proximal section 158 and first distal section 166. In order to prevent kinks, or relatively severe bends, from forming at junctions between unbraided PEBAX tubes and antenna section 162, PEBAX tubes are bonded to shrink tubing 330 using an adhesive connection.

In one embodiment, electrode rings 186 each have a width of approximately one millimeter, although the width of each electrode ring 186 may vary. The material used to form electrode rings 186 may be a material such as stainless steel, although other biocompatible materials, which include iridium platinum, may also be used to form electrode rings 186. Typically, the location of electrode rings 186 on second proximal section 158 and first distal section 166 is such that electrode rings 186 are relatively close to antenna section 162. By way of example, electrode ring 186b may be located such that the edge of electrode ring 186b that is closest to antenna section 162 is approximately five millimeters from antenna section 162. Similarly, electrode ring 186c may be located such that the edge of electrode ring 186b that is closest to antenna section 162 is approximately five millimeters from antenna section 162. The spacing between adjacent electrode rings 186, i.e., the spacing between electrode rings 186a, 186b and the spacing between electrode rings 186c, 186d, may be approximately two millimeters.

A sensor conduit 336, which may be a Teflon tube, carries electrode wires 338, from electrodes 186c, 186d, towards the proximal area of the catheter. Electrode wires 338 may be stainless steel wires that are coated, or otherwise insulated. Sensor conduit 336 may be located along the longitudinal axis of the overall catheter, and, therefore, the longitudinal axis of antenna section 162. That is, sensor conduit 336 is located such that it is substantially parallel to the longitudinal axis of antenna section 162. Further, sensor conduit 336 is generally located within antenna 188, e.g., in the space defined within the coils of antenna 188. As such, sensor conduit 336 may serve to prevent electrode wires 338 from shorting out against antenna 188. Electrode wires 342 associated with electrodes 186a, 186b are generally not carried within a sensor conduit, although the use of a sensor conduit to carry electrode wires 342 may be implemented if desired. Like electrode wires 338, electrode wires 342 may be stainless steel wires which are slightly insulated. In the described embodiment, electrode wires 342 are carried towards the proximal end of the catheter in a spaced defined between tube 332a and shrink tubing 330.

Figure 4A:
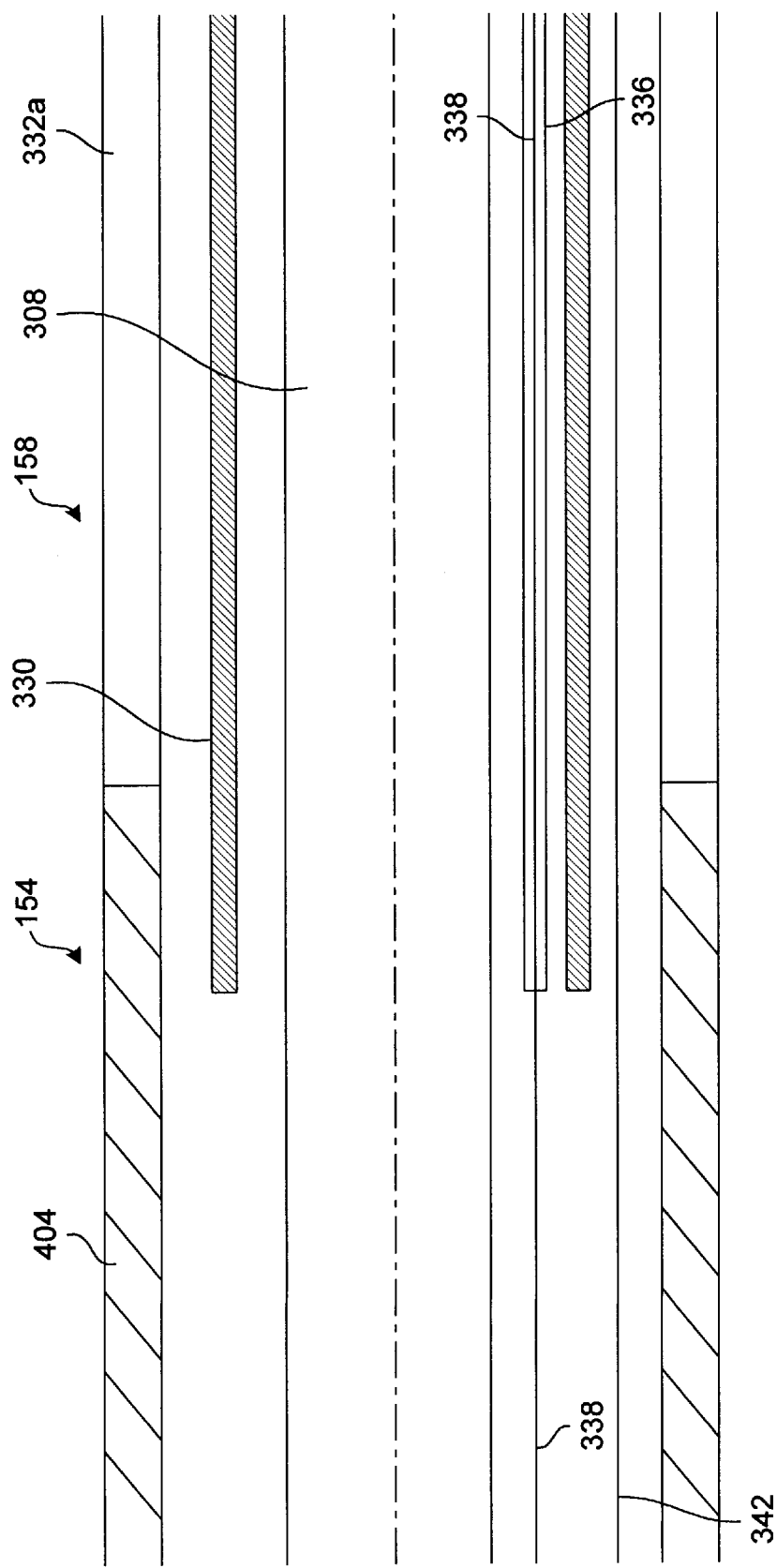
FIG. 4a is a diagrammatic longitudinal cross-sectional representation of an interface between a first proximal section of a catheter and a second proximal section of the catheter, e.g., first proximal section 154 and second proximal section 158 of catheter 150 of FIG. 1, in accordance with the first embodiment of the present invention.

Referring next to FIG. 4a, the internal structure of the interface between a first proximal section of a catheter and a second proximal section of the catheter, e.g., first proximal section 154 and second proximal section 158 of catheter 150 of FIG. 1, will be described in accordance with the first embodiment of the present invention. Transmission line 308, which may be a coaxial cable as described above, is disposed within both first proximal section 154 and second proximal section 158. As transmission line 308 is arranged to be coupled to a power source which is typically external to the overall catheter, transmission line 308 extends through substantially the entire length of first proximal section 154. Shrink tubing 330 extends through the entire length of second proximal section 158, and slightly into first proximal section 154. In one embodiment, shrink tubing 330 extends approximately one centimeter past the "transition" between first proximal section 154 and second proximal section 158. Like transmission line 308, electrode wires 342, 338 extend through substantially the entire length of first proximal section 152. Sensor conduit 338, however, may extend only as far as shrink tubing 336.

As described above, second proximal section 158 may be formed from a PEBAX tube 332a, or shaft. First proximal section 154 may also be formed from a PEBAX tube 404, although PEBAX tube 404 typically differs, e.g., differs structurally, from PEBAX tube 332a. Specifically, tube 404 is generally less flexible, or more stiff, than tube 332a. In one embodiment, tube 404 may have a durometer of approximately seventy Shore D, while tube 332a may have a durometer of approximately forty Shore D. Tube 404 generally includes braid wires arranged to allow tube 404 to sustain torque. By way of example, tube 404 may include stainless steel braid wires.

While a variety of different methods may be used to effectively "connect" tube 404 to tube 332a, one method that is used to connect tube 404 to tube 332a involves heat fusion. In other words, the ends of tubes 332a, 440 may be heated and pressed together to form a fused bond. The use of a heated fusion process is particularly useful when the general materials used in the formation of tubes 332a, 440 is essentially the same. Alternatively, in lieu of a heated fusion process, the ends of tubes 332a, 440 may instead be connected using an adhesive bond.

Figure 4B:
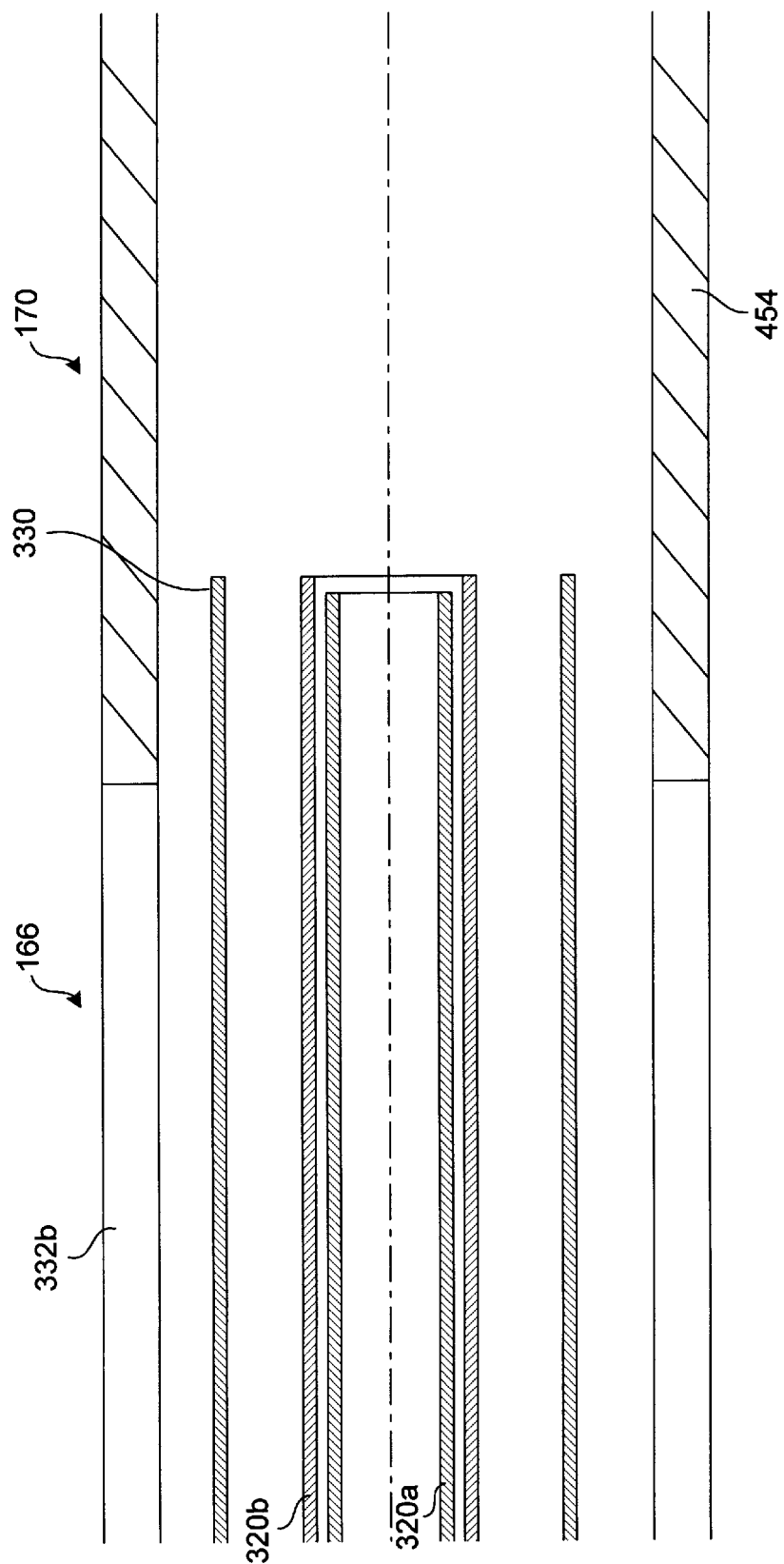
FIG. 4b is a diagrammatic longitudinal cross-sectional representation of an interface between a first distal section of a catheter and a second distal section of the catheter, e.g., first distal section 166 and second distal section 170 of catheter 150 of FIG. 1, in accordance with the first embodiment of the present invention.

The interface between a first distal section of a catheter and a second distal section of the catheter is similar to the interface between a first proximal section of the catheter and a second proximal section of the catheter. However, the underlying structure of the catheter near the interface between the first distal section and the second distal section typically varies from the interface between the first proximal section and the second proximal section. FIG. 4b is a diagrammatic representation of an interface between a first distal section of a catheter and a second distal section of the catheter, e.g., first distal section 166 and second distal section 170 of catheter 150 of FIG. 1, in accordance with the first embodiment of the present invention. Shrink tubing 330, and tubes 320a, 320b are arranged to extend through first distal section 166 and slightly into, e.g., approximately one centimeter into, second distal section 170. It should be appreciated, however, that in some embodiments, tubes 320a, 320b may extend throughout the length of second distal section 170. Tubes 320a, 320b are arranged to provide stiffness to first distal section 166 to "match" the stiffness of second proximal section 158, as discussed above.

First distal section 166 may be formed from a PEBAX tube 332b. Second distal section 170 may also be formed from a PEBAX tube 454 that may differ structurally from PEBAX tube 332b. In the described embodiment, tube 454 is less flexible, or more stiff, than tube 332b. The additional stiffness in tube is effectively generated by integrating braid wires into tube 454. That is, tube 454 may be formed to incorporate stainless steel braid wires such that tube 454 has a higher level of stiffness than tube 332b. As such, the stiffness of second distal section 170 is approximately the same as that of first proximal section 154, as described above with reference to FIG. 4a, despite the fact that transmission line 308 passes through first proximal section 154. The overall stiffness of first proximal section 154 is predominantly due to braid wires in first proximal section 154. Therefore, since second distal section 170 also includes braid wires, the stiffnesses of second distal section 170 and first proximal section 154 are effectively the same.

Since tubes 332b and 454 are made primarily from the same material, e.g., PEBAX, the ends of tubes 332b and 454 may be connected together using a process such as heat fusion. It should be appreciated, however, that rather than implementing a heat fusion process to bond the end of tube 332b to the end of tube 454, the ends of tubes 332b and 454 may be bonded using any suitable adhesive, such as an adhesive that is biocompatible. The use of heat fusion, however, is generally preferred as a fused interface between first distal section 166 and second distal section 170 further prevents kinks from appearing in the overall catheter when forces are applied on the catheter in order to induce curvature.

Figure 5:
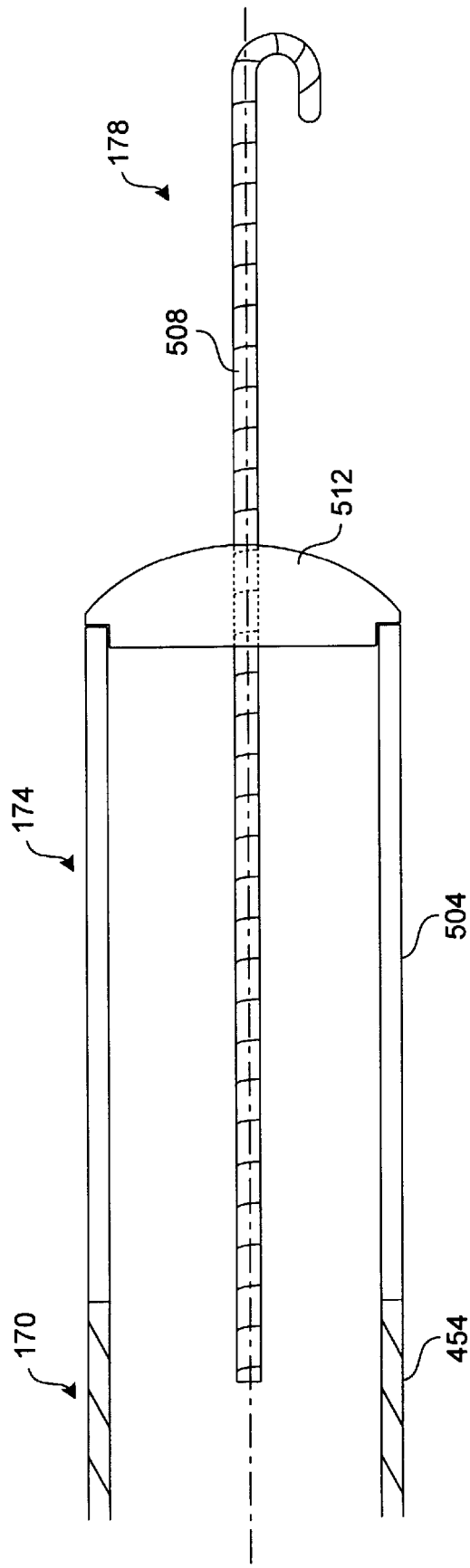
FIG. 5 is a diagrammatic longitudinal cross-sectional representation of a third distal section of a catheter and a tip section of the catheter, e.g., third distal section 174 and tip section 178 as shown in FIG. 1, in accordance with the first embodiment of the present invention.

FIG. 5 is a diagrammatic representation of a third distal section of a catheter and a tip section of the catheter, e.g., third distal section 174 and tip section 178 as shown in FIG. 1, in accordance with the first embodiment of the present invention. As discussed above, second distal section 170 may be formed from a PEBAX tube 454 that is reinforced with braided wires. Third distal section 174, which is preferably more flexible than second distal section 170, may be a PEBAX tube 504 which is not reinforced with braided wires. By way of example, PEBAX tube 504 may be similar to PEBAX tube 332b of FIG. 4b.

As shown, tip section 178 is a spirally wound wire structure 508 with a hooked end that is arranged to be snared. Specifically, in one embodiment, wire structure 508 may be formed from a substantially straight wire that has a coiled wire wrapped around it. While the overall length, or total length, wire structure 508 may vary, wire structure generally extends in the range of approximately eight centimeters to approximately twelve centimeters past the distal end of third distal section 504. Wire structure 508 generally extends the length of third distal section 174 and into second distal section 170. In addition, wire structure 508 is typically secured with respect to third distal section 174. While the length of the portion of wire structure 178 that extends into second distal section 170 may vary, wire structure 508 generally extends at least 0.5 centimeters past the proximal end of third distal section 174, to enable wire structure 508 to be secured to third distal section 174 and to prevent inking in third distal section 174.

In general, an adhesive bond 512 may be formed at the distal end of third distal section 174 to secure wire structure 178. Any suitable adhesive may generally be used to form adhesive bond 512. For instance, suitable adhesives include, but are not limited to, adhesives which are cured using ultraviolet wavelengths, e.g., ultraviolet cure adhesives that are available commercially from Dymax of Mount Prospect, Ill.

Figure 6A:
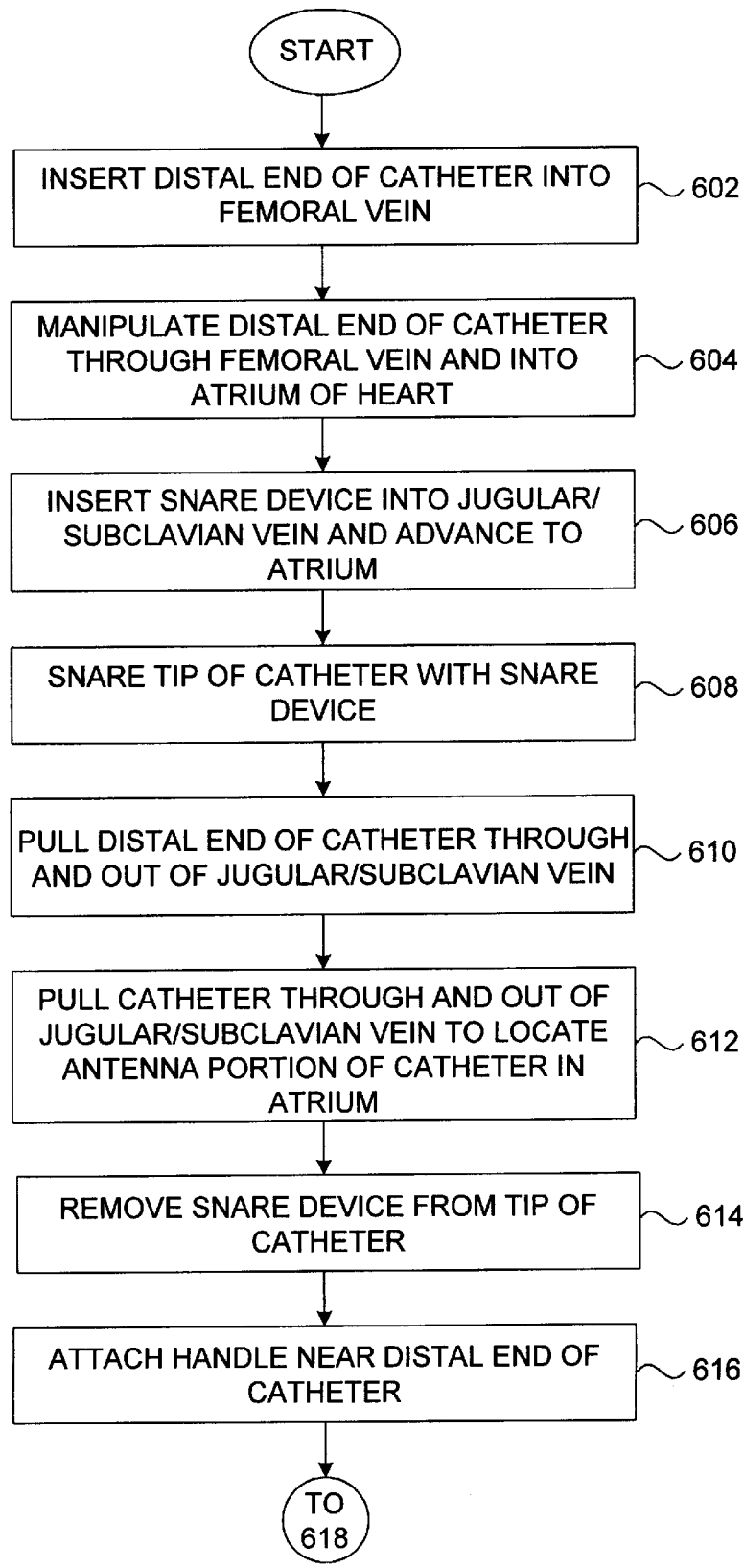
FIGS. 6a and 6b are a process flow diagram which illustrates the steps associated with the use of a loop catheter in accordance with an embodiment of the present invention.
Figure 6B:
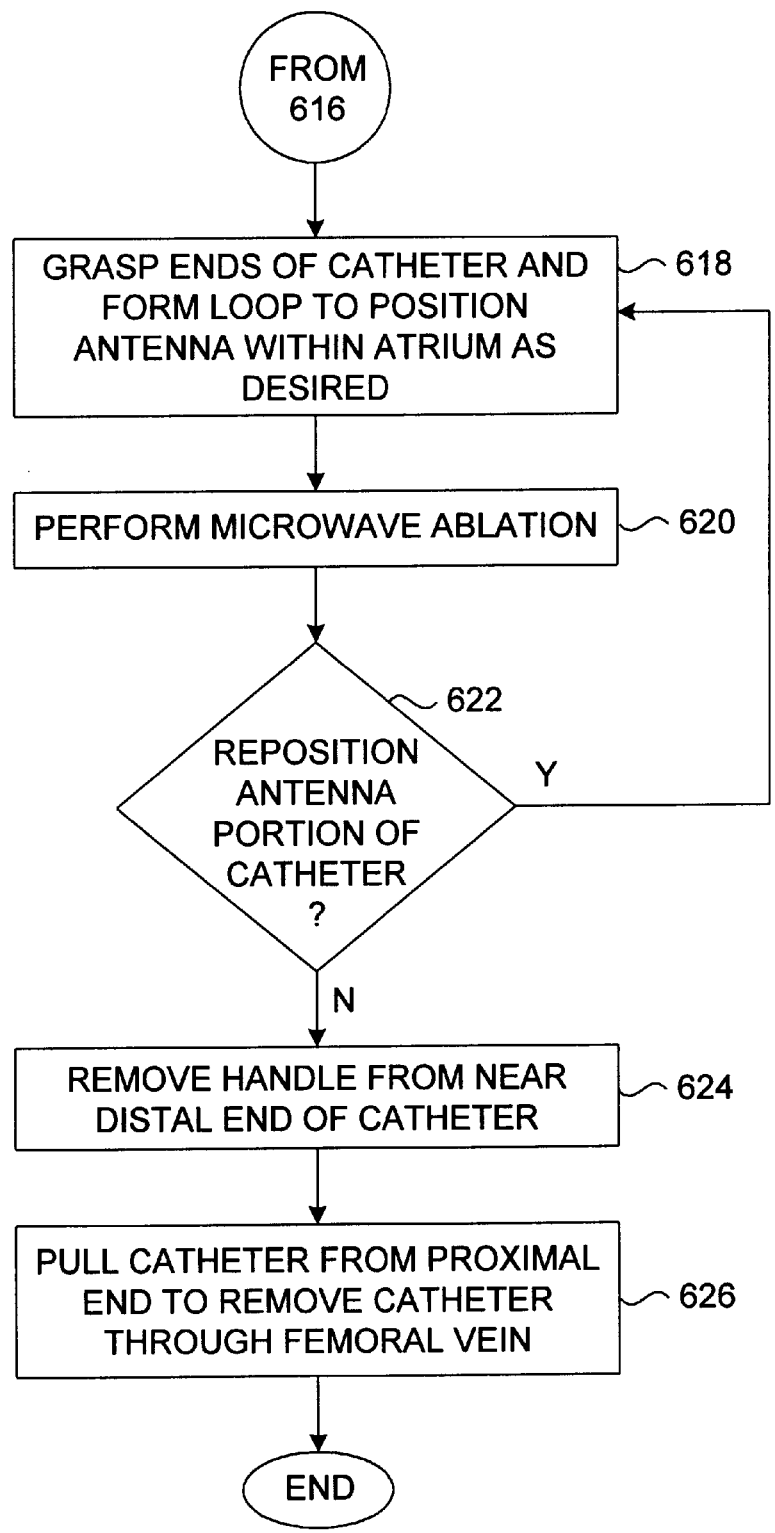

A flexible catheter that has an antenna section which may be arranged to form part of a loop is may be used in a variety of different ways. As discussed above, a loop may be formed against the wall of a cardiac chamber to facilitate the ablation of cardiac tissue. The methods for using such a loop catheter may generally be widely varied. With reference to FIGS. 6a and 6b, the steps associated with one method of using a loop catheter to perform a microwave ablation procedure will be described. Specifically, one method of using a snarable loop catheter will be described in accordance with one embodiment of the present invention. The method begins at step 602 in which the distal end of the loop catheter is inserted into a vein, e.g., a femoral vein, of a patient. Once the distal end of the catheter is inserted into the femoral vein, the distal end of the catheter is manipulated through the femoral vein, and into a cardiac chamber, e.g., the right atrium, of the heart of the patient in step 604. Specifically, the distal end of the catheter is typically moved through the inferior vena cava. Substantially any method may be used in the manipulation of the catheter through the femoral vein and into the atrium of the heart. In the described embodiment, the distal end of the catheter is manipulated just into the atrium, although the distal end of the catheter may instead be manipulated past the atrium and into either the jugular or subclavian vein. It should be appreciated, however, that the catheter may generally be fed through the any suitable vessel and into an appropriate region of the heart, i.e., into the region of the heart in which a microwave ablation procedure is to take place.

A snare device, such as an Amplatz gooseneck snare, available commercially from Microvena of White Bear Cave, Minn., is inserted into either the jugular vein or the subdlavian vein in the neck or shoulder of the patient in step 606. The snare device is fed through either the jugular or the subclavian vein until the tip of the catheter may be snared, or otherwise engaged, by the snare device in step 608. When the distal end of the catheter is in the atrium, the snare device is advanced into the atrium. In one embodiment, the tip of the catheter is a J-hook wire, as described above, that protrudes past the distal end of the catheter. Hence, snaring the J-hook wire effectively snares the tip of the catheter.

After the tip of the catheter is snared, the snare is used in step 610 to effectively pull the catheter through and out of either the jugular vein or the subclavian vein. Enough of the catheter is pulled out of either the jugular or the subdlavian vein to enable the antenna portion, or section, of the catheter to be located within the atrium of the heart. Once the antenna portion of the catheter is located within the atrium of the heart, the snare device is removed from the tip of the catheter in step 614.

To facilitate the gripping of the catheter, in the described embodiment, a handle is attached near the distal end of the catheter in step 616. It should be understood that the handle is not attached until after the distal end of the catheter is pulled out of either the jugular or the subelavian vein. While the configuration of such a handle may vary widely, one suitable handle will be described below with reference to FIGS. 8a–d. The ends of the catheter are then grasped by a user, i.e., the individual who is performing the microwave ablation procedure, in step 618, and a loop is formed in the catheter in order to position the antenna within the atrium as desired. In general, such a loop may be formed through curvature in the antenna portion of the catheter, as well as the two unbraided sections which are on both sides of the antenna portion. As will be appreciated by those skilled in the art, the proximal end of the catheter typically includes a handle. Therefore, grasping the ends of the catheter generally involves grasping handles at the proximal end and the distal end of the catheter.

By effectively applying a force on at least one end of the catheter, the size of a loop formed in the catheter may be varied. In other words, the approximate diameter of the loop formed from the antenna portion and the unbraided portions of the catheter may be varied depending upon how much "pushing" force and "pulling" force is imparted on or near the ends of the catheter. For example, pushing on the ends of the catheter may generally increase the size of a loop formed in the catheter, while pulling on the ends of the catheter may generally decrease the size of a loop formed in the catheter. In addition, torque on one or both ends of the catheter moves the antenna radially around the walls of the atrium, or rotates the antenna about a center point. The application of torque is effective in enabling the antenna to be positioned in substantially any directional orientation within the atrium.

After a loop is formed such that the antenna portion of the catheter is aligned as desired in step 618, process flow proceeds to step 620 in which a microwave ablation procedure is performed. By way of example, tissue may be ablated, or an arrhythmia circuit in the atrium may be cut. Once the microwave ablation procedure is performed, it is determined in step 622 whether the antenna portion of the catheter is to be repositioned within the atrium, or any other part of the heart, in order to perform another procedure, e.g. in order to cut another arrhythmia circuit. It should be appreciated that in some cases, more than one ablation may be necessary in order to effectively cut a single circuit.

When it is determined that it is necessary to reposition the antenna portion of the catheter, then process flow returns to step 618 in which the ends of the catheter are effectively manipulated to position the antenna as desired. Alternatively, if the determination is that the antenna portion of the catheter is not to be repositioned, the catheter may then be prepared for removal for the body of the patient. Accordingly, process flow proceeds to step 624 in which the handle that was attached near the distal end of the catheter is removed. Once the handle is removed, the catheter may then be pulled from its proximal end in step 626 in order to remove the catheter through the femoral artery. After the catheter is removed, the use of the loop catheter to perform microwave ablation is completed.

A loop catheter, e.g., catheter 150 of FIG. 1, may generally be made using materials other than silicone and PEBAX. By way of example, a loop catheter may be fabricated using a material such as polyethylene. When polyethylene is used in the formation of a loop catheter or, more specifically, when polyethylene tubing is used in the formation of a catheter, the densities of the polyethylene may be varied at different portions of the catheter in order to vary the stiffness of the catheter. In other words, a higher density in polyethylene is generally associated with a higher stiffness, while a lower density in polyethylene is generally associated with a lower stiffness. Varying the stiffness of the catheter by varying the densities of the polyethylene may eliminate the need to add internal structures, e.g., internal tubing, to the catheter in order to achieve desired stiffnesses at different portions of the catheter.

For a loop catheter which is formed using polyethylene, the densities of the polyethylene in different areas may be varied such that the flexibility of the catheter is similar to the flexibility of catheter 150 of FIG. 1. That is, catheter 150 of FIG. 1 may be formed from a material such as polyethylene. Specifically, the stiffniess of polyethylene used in a first proximal section may be substantially the same as the stiffness of polyethylene used in a second distal section of a catheter, while the stiffness of polyethylene used in a second proximal section may be substantially the same as the stiffness of polyethylene used in a first distal section. As was the case with catheter 150 of FIG. 1, the stiffnesses in the first proximal section and the second distal section of a catheter formed from polyethylene are generally greater than the stiffnesses in the second proximal section and the first distal section of the catheter. Further, the stiffniess of the antenna section of the catheter is generally less than the stiffnesses in the second proximal section and the first distal section. Hence, the antenna portion is typically more flexible than the second proximal section and the first distal section.

For a catheter formed from polyethylene, the diameters of the different sections of the catheter may vary from the diameters of catheter 150 of FIG. 1. By way of example, the outer diameters of different sections of a catheter formed from polyethylene may range from approximately five French to approximately nine French, i.e., from approximately 0.066 inches to approximately 0.141 inches. In one embodiment, the outer diameter of a first proximal section may be approximately 8.5 French, while the outer diameter of a second proximal section may be approximately eight French. The outer diameter of an antenna section in such an embodiment may be approximately eight French, while a first distal section may have an outer diameter of approximately eight French. Finally, the outer diameters of a second distal section and a third distal section may be approximately 7.5 and eight French, respectively.

In order to maintain substantially the same stiffness in the first proximal section of a catheter and the second distal section of the catheter, since the first proximal section generally has a transmission line disposed therein, the density of polyethylene in the second distal section may be higher than the density of polyethylene in the first proximal section. Similarly, due to the presence of a transmission line, the density of polyethylene used in the formation of the second proximal section may be lower than the density of polyethylene used in the formation of the first distal section.

Figure 7:
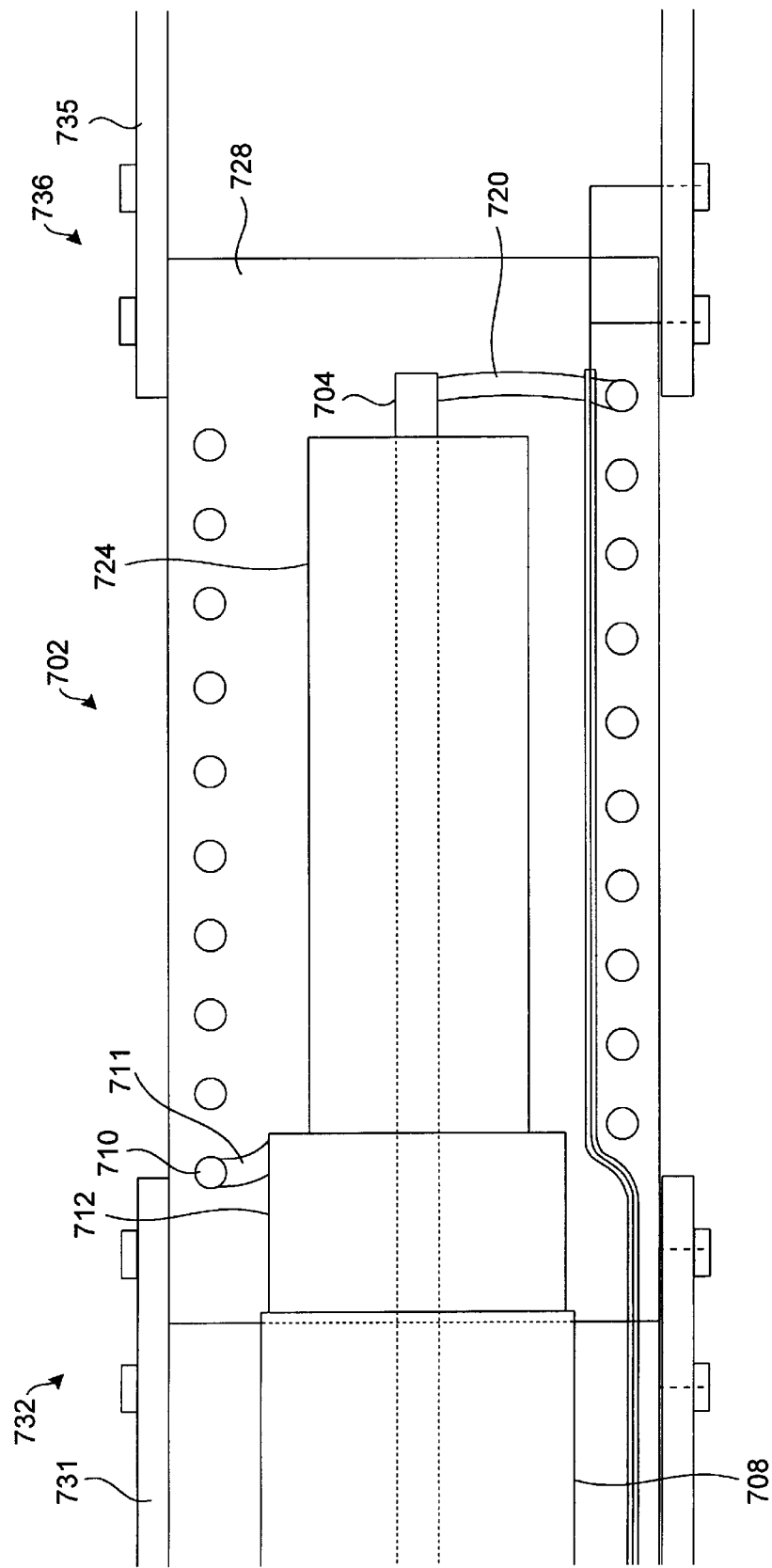
FIG. 7 is a diagrammatic longitudinal cross-sectional representation of an antenna portion of a loop catheter in accordance with a second embodiment of the present invention.

FIG. 7 is a diagrammatic longitudinal cross-sectional representation of an antenna portion of a loop catheter formed using polyethylene in accordance with a second embodiment of the present invention. It should be appreciated that for illustrative purposes, antenna section 702 and components of the overall loop catheter that are located within antenna section 702, have not been shown to scale. For instance, the relative sizes of some components within antenna section 702 have been exaggerated for illustrative purposes. Antenna section 702 includes a center conductor 704 which is part of a transmission line 708. In one embodiment, transmission line 708 may be a coaxial cable. Transmission line 708 may be coupled to a power supply that is external with respect to the overall catheter. The dimensions of transmission line 708 may vary depending upon the requirements of a particular loop catheter for. By way of example, the outer diameter of transmission line 708 may vary in the range of approximately 0.10 to approximately 0.15 centimeters.

Antenna section 702 includes an antenna 710, which is typically in the form of a coil. A proximal end 711 of antenna 710 is grounded to a shield 712 of transmission line 708, while a distal end 720 of antenna 710 is attached to center conductor 704 to enable power to be provided to antenna 710. Antenna 710 may be made from any suitable material, as for example spring steel, beryllium copper, or silver-plated copper. When antenna 710 is a coil such as a helical coil, the outer diameter of antenna 710 may vary depending upon the particular application of the catheter. For atrial fibrillation applications, antenna 710 may be a helical coil with an outer diameter in the range of approximately 0.15 to approximately 0.4 centimeters. The overall length of antenna 710, in addition to the number of turns in antenna 710, may also vary. By way of example, the coiled length of antenna 710 may be in the range of approximately two to approximately six centimeters in length. In one embodiment, the number of turns in antenna 710, while shown as being relatively small for ease of illustration, may be in the range of approximately sixty to approximately one hundred turns.

Within antenna section 702, center conductor 704 is substantially encased in a dielectric material 724 to prevent center conductor 704 from coming into contact with shield 712. In the described embodiment, a polyethylene "cap" 728 is formed over antenna 710, center conductor 704, shield 712, and dielectric material 724, as shown. Cap 728 allows antenna section 702 to be fused, e.g., heat fused, to a polyethylene tube 731 of second proximal section 732 and a polyethylene tube 735 of a first distal section 736. That is, cap 728 is fused to polyethylene tubes 731, 735 using any suitable heat fusion process. The use of a heat fused bond may reduce kinking, that may be associated with adhesive bonds, in the overall loop catheter when a loop that includes antenna section 702 is formed. To allow a heat fused bond to be readily formed, cap 728 generally extends into both second proximal section 732 and first distal section 736, e.g., by approximately five millimeters, on each end.

When a catheter, e.g., catheter 150 of FIG. 1, is used to perform ablation in a heart, certain portions of the heart may prove to be difficult to reach. By way of example, the shape and size of the right side of the right atrium of the heart often includes crevices such as the atrial appendage that make it difficult to orient the antenna portion of the catheter against the cardiac wall as needed. In order to alleviate such orientation problems, a hinge device may be included in a catheter to facilitate the orientation of the antenna portion of the catheter. Such a hinge device may serve to allow a loop to be formed that is "flatter" in some sections to enable positioning in difficult to reach areas, e.g., corners. FIG. 9*a* is a diagrammatic representation of a loop catheter that includes a hinge device in accordance with an embodiment of the present invention. A catheter 950 includes a first proximal section 954, a second proximal section 958, an antenna section 962, a first distal section 966, a second distal section 970, a third distal section 974, and a tip section 978. In the described embodiment, with the exception of first distal section 966, the remaining sections of catheter 950 are similar to the corresponding sections of catheter 150 as described above with reference to FIG. 1. For purposes of illustration, it should be appreciated that the relative dimensions of the different sections of catheter 950 have not been shown to scale.

First distal section 966, which may be approximately two centimeters to approximately five centimeters in length, includes a hinge 980. Hinge 980 may be formed from substantially any biocompatible material including, but not limited to, stainless steel and assorted polymers such as polypropylene, polycarbonate, and polyethylene. In one embodiment, hinge 980 may be arranged to allow for rotation about a single axis, although it should be appreciated that hinge 908 may instead be arranged to enable rotation in more than one plane. By way of example, hinge 980 may be similar to a ball-and-socket joint. Preferably, hinge 980 rotates about a single axis, as such rotation allows torque to transmit through hinge 980 and is generally easier to control than a ball-and-socket joint.

Hinge 980 allows the shape of a loop formed in catheter 950 to be varied from a substantially rounded shape, as will be described below with respect to FIG. 9b. Specifically, hinge 980 allows antenna section 962 to be flattened against a cardiac wall, and further may allow corners or crevices in a heart to be more easily accessed by antenna section 962 for ablation. Hinge 980 is arranged such that it may be rotated when a torque or axial force is applied near an end of catheter 950, e.g., at a handle 982 of catheter 950 or near the overall distal end of catheter 950.

Figure 9B:
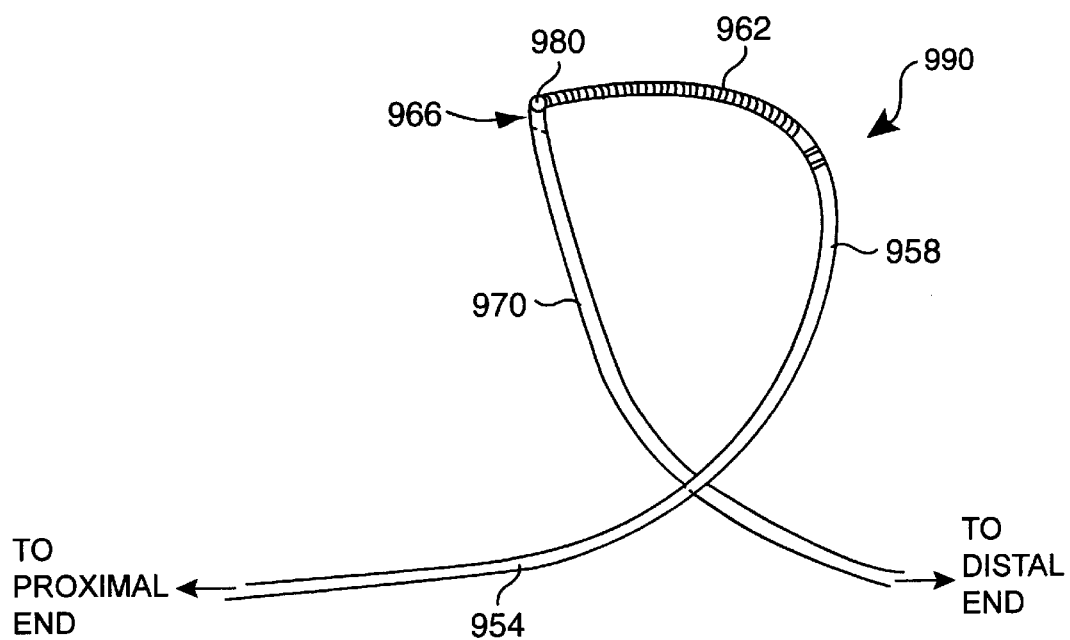
FIG. 9b is a diagrammatic close-up representation of the looped portion of a catheter that includes a hinge, e.g., catheter 950 of FIG. 9a, in accordance with the fourth embodiment of the present invention.

FIG. 9b is a diagrammatic close-up representation of a loop that may be formed in catheter 950 to include antenna section 962. A loop 990 is formed from antenna section 962, second proximal section 958, first distal section 966, and second distal section 970. As discussed above, first distal section 966 includes hinge 980. The curvature of loop 990 is varied throughout loop 990, as hinge 980 permits an effective "sharp" bend to be formed in loop 990. In general, the overall curvature associated with loop 990, or, more specifically, the sharpness of the bend associated with hinge 980, may be varied by varying the force and torque applied at or near the ends of catheter 950.

As mentioned above, in order to facilitate the formation of a loop in a loop catheter, a handle may be provided for use with the loop catheter. Specifically, a detachable handle, which is arranged to be mounted near the distal end of the loop catheter, may be provided for use in conjunction with a handle that is typically fixably attached near the proximal end of the loop catheter. In general, the configuration of a handle which may be mounted near the distal end of a loop catheter may be widely varied. Suitable handles may be arranged such that they may be mounted on the catheter without damaging the catheter, or, more specifically, the tubing of the catheter.

Figure 8A:
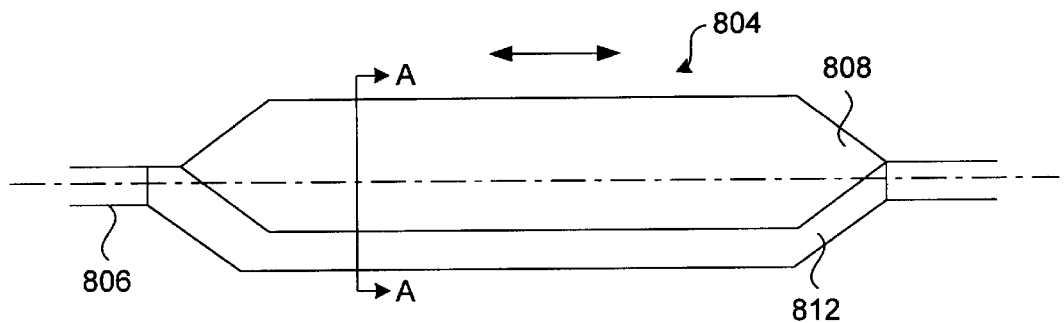
FIG. 8a is a diagrammatic side-view representation of a handle that is suitable for use with a loop catheter in accordance with a third embodiment of the present invention.
Figure 8B:
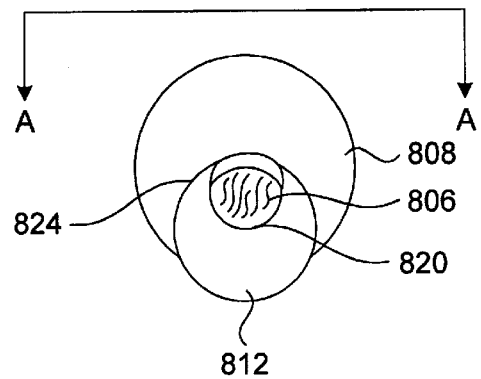
FIG. 8b is a diagrammatic cross-sectional axial representation of a handle, i.e., handle 804 of FIG. 8a, in accordance with the third embodiment of the present invention.
Figure 8C:
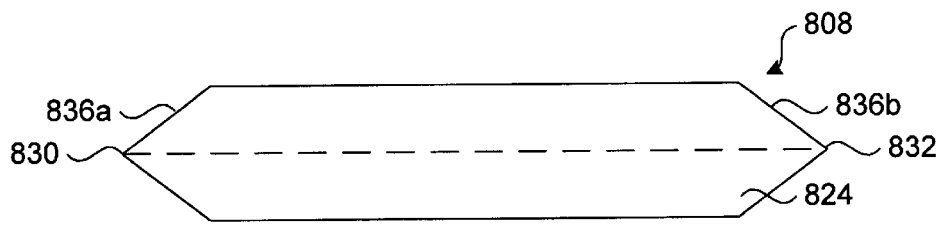
FIG. 8c is a diagrammatic side-view representation of a cap component of a handle, i.e., cap component 808 of FIG. 8a, in accordance with the third embodiment of the present invention.
Figure 8D:
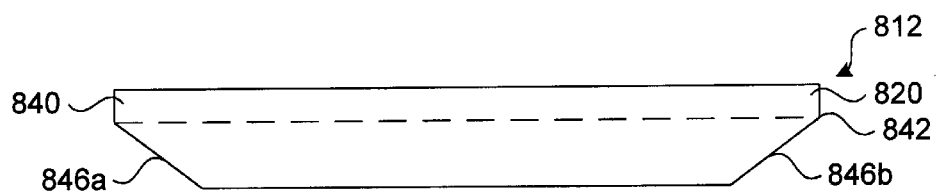
FIG. 8d is a diagrammatic side-view representation of a base component of a handle, i.e., base component 812 of FIG. 8a, in accordance with the third embodiment of the present invention.

One suitable handle that may be used in conjunction with a loop catheter is a handle that may be slidably attached and detached from the catheter, as will be described with reference to FIGS. 8a–8d. FIG. 8a is a diagrammatic side-view representation of a detachable handle in accordance with a third embodiment of the present invention, while FIG. 8b is a diagrammatic cross-sectional axial representation of the handle. FIGS. 8c and 8d are diagrammatic side-view representations the components of the handle. As shown in FIG. 8a, a handle 804 is arranged to be mounted on a catheter 806 such that handle 804 is aligned along a longitudinal axis of catheter 806. When handle 804 is to be mounted over, or around, catheter 806, catheter is first placed in a groove 820 of base component 812.

Groove 820, as shown in FIG. 8b, is arranged to securely accommodate catheter 806. In other words, groove 820 is sized such that catheter 806 may be held within groove 820 without being damaged. As such, the curvature present in the bottom of groove 820 is sized so that the curvature has a radius that is approximately the same as the radius of catheter 806 or, more specifically, the radius near the portion of catheter 806 where handle 804 is to be placed. By way of example, when catheter 806 has a diameter of approximately 0.100 inches , e.g., approximately eight French, the diameter of the bottom of groove 820 may be approximately 0.097 inches to approximately 0.099 inches. That is, the bottom of groove 820 may have a diameter that is in the range of approximately 0.001 inches to approximately 0.003 inches less than the diameter of the portion of catheter 806 that is to be inserted in the bottom of groove 820. Such a difference in diameters enables catheter 806 to be relatively securely held without damaging catheter 806.

Once catheter 806 is securely placed in, e.g., lightly press-fit into, base component 812, a cap component 808 is slidably moved over base component 812, and aligned such that catheter 806 is held between cap component 808 and base component 812. Cap component 808 includes a groove 824 that is arranged to be slid over base component 812. Groove 824 is typically sized such that groove 824 may slide over base component 812. In one embodiment, when base component has 812 has an overall external diameter of approximately 0.250 inches, then groove 824 may have an approximate diameter of 0.250 inches to approximately 0.251 inches. It should be appreciated, however, that the size of base component 812 and, hence, the size of groove 824, may generally be widely varied.

The slide-fit between cap component 808 and base component 812 is such that sliding motion is possible between cap component 808 and base component 812 in a longitudinal direction, when a translational force is applied to cap component 808. The slide-fit generally does not enable cap component 808 to become detached, or disengaged, from base component 812 when no translational force is applied to cap component 808. In one embodiment, handle 804 is designed such that cap component 808 may be detached from base component 812 substantially only by causing cap component 808 to slide longitudinally with respect to base component 812. That is, cap component 808 engages base component 812 to prevent non-longitudinal translational movement of catheter 806 with respect to handle 804, such as movement of catheter 806 out of groove 820.

In general, the material from which handle 804 is formed may be widely varied. Suitable materials are generally relatively lightweight, relatively easy to machine or mold, and durable, or strong. By way of example, a lightweight, strong material such as polyacetal may be used to form cap component 808 and base component 812. Additionally, the size of cap component 808 and base component 812 may also vary, depending upon factors which may include, but are not limited to, the size of catheter 806 and the requirements of the overall catheter system. By way of example, the length of cap component 808, measured between tips 830 and 832 of cap component 808, may be in the range of approximately 2.6 to approximately 2.8 inches, while the length of base component 812, measured between tips 840 and 842 of base component 812, may be in the range of approximately 2.7 to approximately 2.9 inches. It should be appreciated that the lengths of cap component 808 and base component 812 may also be much smaller and much larger. Similarly, the curvature, e.g., approximate diameters, associated with cap component 808 and base component 812 may also vary widely. For example, the approximate diameter of cap component 808 may be in the range of approximately 0.3 to approximately 0.5 inches, while the approximate diameter of base component 812 may be in the range of approximately 0.2 to approximately 0.3 inches. In one embodiment, the dimensions of cap component 808 and base component 812 may be chosen such that the center of catheter 806 is approximately centered with respect to the outer diameter of cap component 808 when handle 804 is assembled.

Cap component 808 and base component 812 may be fabricated using a variety of different processes. For example, cap component 808 and base component 812 may be formed from rods of a material such as polyacetal. The ends of the rods may be shaped on a lathe to form tapered edges, e.g., edges 836 and 846. Grooves 824, 820, may then be milled out of the rods to form cap component 808 and base component 812, respectively.

Although only a few embodiments of the present invention have been described, it should be understood that the present invention may be embodied in many other specific forms without departing from the spirit or scope of the present invention. By way of example, although the invention has been described in terms of an ablation catheter that may be formed into a loop for cardiac applications, it should be appreciated that the ablation loop catheter may be used for a wide variety of non-cardiac ablation applications as well. In addition, while the ablation loop catheter has been described as using a microwave ablating energy source, the ablation loop catheter may be used, or adapted for use, with other types of ablating energy sources as well. Other ablating energy sources include, but are not limited to, ablating sources which utilize radio frequency energy, ultrasound, or cryogenics.

The formation of a loop that includes the antenna portion of a catheter has generally being described as occurring in a cardiac chamber such as an atrium of the heart. However, it should be appreciated that a loop may be formed in any other portion of the body of a patient that may require an ablation procedure.

In general, the steps associated with using a loop catheter to perform ablation procedures may vary depending upon factors which include, but are not limited to, the particular configuration of a loop catheter and the overall requirements of a catheter system. Steps may be added, deleted, or reordered, and individual steps may be varied, without departing from the spirit or the scope of the present invention.

While the steps associated with a method of using a loop catheter has been described in terms of snaring the distal end of the loop catheter with a snaring device in order to manipulate the distal end of the catheter out of the body of a patient, it should be appreciated that any number of different methods may be used to manipulate the distal end out of the body of the patient. For example, a guide wire, which is not integrated into the catheter, may be used to effectively "thread" the catheter past a cardiac chamber and out of the body through a vein such as the jugular or subclavian vein. In one embodiment, when a non-integrated guide wire is used, a polyimide tube may extend from the proximal end of a catheter to the distal end of the catheter to allow the catheter to be maneuvered over the guide wire through the center of the antenna.

Another method for using the loop catheter may involve using a guide wire, which is not integrated into the catheter, that effectively threads only a distal end of the catheter. A short tube, e.g., a short polyimide tube, may be located near the distal tip if the catheter to allow the catheter to be maneuvered over the guide wire. Such a tube may be located from the distal tip of the catheter to approximately five to twentyfive centimeters proximal from the distal tip of the catheter.

Further, although a wire fashioned as a J-hook has generally been described for use in allowing the distal end of a catheter to be snared, the structure used to facilitate snaring of the catheter may vary. For instance, a looped wire may be used as a snarable end of a catheter. Alternatively, a notch may be formed near the distal end of the catheter which may be engaged by a snaring mechanism.

Extension tubes which are fabricated from a material such as Teflon or polyethylene are suitable for use in stiffening portions of a catheter, e.g., a second distal section of a catheter. Instead of using extension tubes, however, a variety of other stiffening structures may also be used. One suitable alternative stiffening structure may be a wire that is configured, or properly shaped, to facilitate bending of associated portions of the catheter. In one embodiment, such a wire may be a shape memory wire which returns to an ambient, or "rest," state once force is removed from the catheter.

Additionally, in lieu of forming a loop that includes the antenna, or transducer, portion of the catheter, it should be appreciated that the catheter may also be used in ablation procedures by curving the antenna portion of the catheter without actually forming a loop. In other words, a catheter may be manipulated, and force may be applied from near the ends of the catheter, to cause the antenna portion of the catheter to bend such that a curve is formed in the antenna portion. The curvature formed in the antenna portion may allow the length of the antenna to substantially conform to a cardiac wall. Alternatively, in some cases, the antenna portion of the catheter may even be conformed against a relatively straight surface that is to be ablated while imparting relatively little curvature in the antenna portion without departing from the spirit or the scope of the present invention.

The antenna in a loop catheter has generally been described as being a coiled antenna, or, more specifically, a helically coiled antenna. In general, however, the antenna in a loop catheter may take on a variety of other configurations. The configurations for an antenna may include, but are not limited to, an antenna which is a substantially flat wire and an antenna which has a substantially circular cross-section.

While a catheter has been described as being formed from materials such as Teflon, silicone, PEBAX resins, and polyethylene, substantially any suitable material may be used in the formation of a catheter. Specifically, for portions of the catheter which come into contact with the body of a patient, any biocompatible material with appropriate flexibility properties may generally be used in the formation of the catheter. Similarly, the materials used to form portions of the catheter which are not intended to come into contact with the body of a patient may also vary. By way of example, although Teflon tubes have been described as being used to provide stiffness in different portions of the catheter, other stiffening materials and structures may be used to provide stiffness to the catheter.

Although one detachable handle has been described as being suitable for use near a distal end of a loop catheter, it should be appreciated that other detachable handles, which do not cause damage to the loop catheter, may be used as well. Other suitable handles may include, but are not limited to, handles with pieces which are screwed or otherwise clamped together around the catheter and handles with pieces which are press fit together around the catheter. Therefore, the present examples are to be considered as illustrative and not restrictive, and the invention is not to be limited to the details given herein, but may be modified within the scope of the appended claims.

What is claimed is:

1. A method for medical treatment using an ablation catheter system that includes a catheter having a transmission line disposed within a flexible tubular member and a transducer coupled to the transmission line of the catheter for generating an electric field sufficiently strong to cause tissue ablation, the transducer being located at a central portion of the catheter that is proximal to a distal tip portion of the catheter, the method comprising:

a) introducing the catheter into a first vessel of the body of a patient and past the heart of the patient such that the distal tip portion of the catheter at least partially passes out of the body of the patient through a second vessel while the central portion of the catheter is positioned within a cardiac chamber of the heart of the body of the patient;

b) forming curvature in the catheter within the cardiac chamber of the heart of the body of the patient, the curvature including the central portion of the catheter; and c) applying electromagnetic energy to the transmission line to cause ablation of cardiac tissue in a region adjacent to the central portion of the catheter.

2. A method for medical treatment as recited in claim 1 further including:

d) modifying the curvature in the catheter within the cardiac chamber of the heart of the body of the patient; and e) repeating steps (c) and (d) to facilitate the ablation of different regions of cardiac tissue.

3. A method for medical treatment as recited in claim 1 wherein forming curvature in the catheter within the cardiac chamber of the heart of the body of the patient includes forming a loop in the catheter within the cardiac chamber of the heart of the body of the patient, the loop including the central portion of the catheter.

4. A method for medical treatment as recited in claim 3 further including:

d) modifying the loop in the catheter within the cardiac chamber of the heart of the body of the patient, wherein modifying the loop includes modifying a size of the loop; and e) repeating steps (c) and (d) to facilitate the ablation of different regions of cardiac tissue.

5. A method for medical treatment as recited in claim 1 wherein introducing the catheter into the first vessel of the body of the patient and past the heart of the patient such that the distal tip portion of the catheter at least partially passes out of the body of the patient through the second vessel while the central portion of the catheter is positioned within the cardiac chamber of the heart of the body of the patient includes:

positioning the distal portion of the catheter in the second vessel within the body if the patient;

snaring the distal portion of the catheter; and manipulating the snared distal portion of the catheter through the second vessel and out of the body of the patient through the second vessel.

6. A method for medical treatment as recited in claim 5 wherein introducing the catheter into the first vessel of the body of the patient and past the heart of the patient such that the distal tip portion of the catheter at least partially passes out of the body of the patient through the second vessel while the central portion of the catheter is positioned within the cardiac chamber of the heart of the body of the patient further includes:

unsnaring the distal portion of the catheter; and attaching a first handle near the distal portion of the catheter, wherein the first handle is removable.

7. A method for medical treatment as recited in claim 6 wherein the catheter includes a proximal end, the proximal end being arranged to remain outside of the body of the patient when the catheter is introduced into the first vessel of the body of the patient, and forming the curvature in the catheter within the cardiac chamber of the heart of the body of the patient includes:

applying a force to at least one of the first handle and a second handle, the second handle being attached near the proximal end of the catheter, wherein applying the force causes the curvature to be formed in the catheter within the cardiac chamber of the heart of the body of the patient.

8. A method for medical treatment as recited in claim 1 wherein introducing the catheter into the first vessel of the body of the patient and past the heart of the patient such that the distal tip portion of the catheter at least partially passes out of the body of the patient through the second vessel while the central portion of the catheter is positioned within the cardiac chamber of the heart of the body of the patient includes:

monitoring electro-physiological signals using catheter electrodes;

determining an appropriate ablation position based at least in part on the monitored electro-physiological signals; and positioning the transducer at the determined appropriate ablation position.

9. A method for medical treatment using an ablation catheter system that includes a catheter having a transmission line disposed within a flexible tubular member of the catheter and a transducer coupled to the transmission line of the catheter, the transducer being arranged to generate an electric field sufficiently strong to cause tissue ablation, the transducer being located at a central section of the catheter that is proximal to a distal section of the catheter, the method comprising:

introducing a tip of the distal section of the catheter into a first vessel of the body of a patient;

maneuvering the tip of the distal section of the catheter through the first vessel and into a cardiac chamber of the body of the patient;

maneuvering the tip of the distal section of the catheter past the cardiac chamber and into a second vessel of the body of the patient; and maneuvering the tip of the distal section of the catheter through the second vessel such that the central section of the catheter is positioned within the cardiac chamber.

10. A method as recited in claim 9 wherein maneuvering the tip of the distal section of the catheter through the second vessel includes maneuvering the tip of the distal section of the catheter out of the body through the second vessel.

11. A method as recited in claim 10 further including:

imparting a force to at least one of a proximal end of the catheter and the distal section of the catheter, the proximal end of the catheter being proximal to the central section of the catheter, the proximal end of the catheter further being external to the body while the central section of the catheter is positioned within the cardiac chamber.

12. A method as recited in claim 11 wherein imparting the force to at least one of the proximal end of the catheter and the distal section of the catheter causes a curvature to be formed in the central section of the catheter.

13. A method as recited in claim 12 further including:

applying electromagnetic energy to the transmission line to cause ablation of cardiac tissue in a region of the cardiac chamber that is adjacent to the central section of the catheter.

14. A method as recited in claim 1 wherein imparting the force to at least one of the proximal end of the catheter and the distal section of the catheter causes a loop to be formed in the catheter, the loop including at least a first portion of the central section of the catheter.

15. A method as recited in claim 14 further including:

applying electromagnetic energy to the transmission line to cause ablation of cardiac tissue in a region of the cardiac chamber that is adjacent to the first portion of the central section of the catheter that includes the loop, the transducer being at least partially located in the first portion of the central section of the catheter.

16. A method as recited in claim 10 wherein the tip of the distal section of the catheter includes a snarable arrangement, and maneuvering the tip of the distal section of the catheter out of the body through the second vessel such that the central section of the catheter is positioned within the cardiac chamber includes snaring the snarable arrangement.

17. A method as recited in claim 16 wherein snaring the snarable arrangement includes:

introducing a snaring device into the second vessel; and engaging the snarable arrangement with the snaring device.

18. A method as recited in claim 17 further including manipulating the snaring device through the second vessel while the snarable arrangement is engaged by the snaring device.

19. A method as recited in claim 18 wherein maneuvering the tip of the distal section of the catheter out of the body through the second vessel such that the central section of the catheter is positioned within the cardiac chamber is substantially accomplished by manipulating the snarable arrangement out of the body through the second vessel using the snaring device.

20. A method as recited in claim 9 further including:

monitoring electro-physiological signals using catheter electrodes, the catheter electrodes being located at the central section of the catheter; and determining an appropriate ablation position based at least in part on the monitored electro-physiological signals.

21. A method as recited in claim 9 wherein maneuvering the tip of the distal section of the catheter through the second vessel includes maneuvering the tip of the distal section of the catheter out of the body through the second vessel, the method further including:

imparting a force on at least one of a proximal end of the catheter and the distal section of the catheter, the proximal end of the catheter being proximal to the central section of the catheter, the proximal end of the catheter further being external to the body while the central section of the catheter is positioned within the cardiac chamber, wherein imparting the force to the at least one of the proximal end of the catheter and the distal section of the catheter causes a curvature to be formed in the central section of the catheter to cause the transducer located at the central section of the catheter to be substantially positioned at the determine appropriate ablation position.

* * * * *